(12) United States Patent
Robarge et al.

(10) Patent No.: US 9,309,262 B2
(45) Date of Patent: Apr. 12, 2016

(54) THIENYLINDOLE AZEPINES AS SEROTONIN 5-HT$_{2C}$ RECEPTOR LIGANDS AND USES THEREOF

(71) Applicant: ABT Holding Company, Cleveland, OH (US)

(72) Inventors: Michael Robarge, Burton, OH (US); Michelle Zawadski, Cleveland, OH (US); John Harrington, Cleveland, OH (US)

(73) Assignee: ABT Holding Company, Cleveland, OH (US)

( * ) Notice: Subject to any disclaimer, the term of this patent is extended or adjusted under 35 U.S.C. 154(b) by 105 days.

(21) Appl. No.: 14/200,875

(22) Filed: Mar. 7, 2014

(65) Prior Publication Data

US 2014/0275035 A1 Sep. 18, 2014

Related U.S. Application Data

(60) Provisional application No. 61/780,424, filed on Mar. 13, 2013.

(51) Int. Cl.
*A61K 31/55* (2006.01)
*C07D 495/14* (2006.01)

(52) U.S. Cl.
CPC .................... *C07D 495/14* (2013.01)

(58) Field of Classification Search
CPC .............................. A61K 31/55; C07D 495/14
USPC ...................... 514/212.02, 215; 540/543, 578
See application file for complete search history.

(56) References Cited

U.S. PATENT DOCUMENTS

| | | | |
|---|---|---|---|
| 4,414,225 | A | 11/1983 | Sauter et al. |
| 4,575,504 | A | 3/1986 | Sauter et al. |
| 4,904,653 | A | 2/1990 | Clark et al. |
| 5,258,378 | A | 11/1993 | Clark et al. |
| 5,532,240 | A | 7/1996 | Nakao et al. |
| 5,691,330 | A | 11/1997 | Nakao et al. |
| 5,998,433 | A | 12/1999 | Takatani et al. |
| 2006/0003990 | A1 | 1/2006 | Bennani et al. |
| 2010/0048537 | A1 | 2/2010 | Matsuoka et al. |
| 2011/0112072 | A1 | 5/2011 | Tumey et al. |

FOREIGN PATENT DOCUMENTS

| | | |
|---|---|---|
| CA | 2104371 | 6/1993 |
| WO | WO 93/13105 | 7/1993 |
| WO | WO 96/11201 | 4/1996 |
| WO | WO 2004/024065 | 3/2004 |
| WO | WO 2005/003096 | 1/2005 |
| WO | WO 2005/019179 | 3/2005 |
| WO | WO 2005/040169 | 5/2005 |
| WO | WO 2005/042490 | 5/2005 |
| WO | WO 2005/042491 | 5/2005 |

OTHER PUBLICATIONS

Bromidge et al., "Novel and selective 5-HT 2C/2B receptor antagonists as potential anxiolytic agents: synthesis, quantitative structure-activity relationships, and molecular modeling of substituted 1-(3-pyridylcarbamoyl)indulines", J. Med. Chem.. 1998, 41, pp. 1598-1612.
Dekeyne et al., "Discriminative stimulus properties of the novel serotonin (5-HT)2C receptor agonist, RO 60-0175: a pharmacological analysis", Neuropharmacology, 38, 1999, pp. 415-423.
International Search Report and Written Opinion issued Jun. 20, 2014 in corresponding International Application No. PCT/US2014/021822.
Glennon, "Serotonin Receptors: Clinical Implications", Neuroscience & Biobehavioral Reviews. vol. 14, 1990, pp. 35-47.
Baxter et al., "5-HT2 receptor subtypes: a family re-united?", TIPS, vol. 16, Mar. 1995, pp. 105-110.
Bos et al., "Novel agonists of 5HT2c receptors. Syntheses and biological evaluation of substituted 2-(indol-1-yl)-1-methylethylamines and 2-(indeno[1,2-b]pyrrol-1-yl)-1-methylethylamines. Improved therapeutics for obsessive compulsive disorder", J. Med. Chem. 40, 1997, pp. 2762-2769.
Martin et al., "5-HT2c receptor agonists: pharmacological characteristics and therapeutic potential", The Journal of Pharmacology and Experimental Therapeutics, vol. 286, No. 2, 1998, pp. 913-924.
Berge et al., "Pharmaceutical salts", Pharmaceutical Sciences, vol. 66, No. 1, Jan. 1977, pp. 1-19.
Higuchi et al., "Pro-drugs as novel drug delivery systems", American Chemical Society, 1975, pp. 1-3.
Roche et al., "Bioreversible carriers in drug design theory and application", American Pharmaceutical Association and Pergamon Press (1987), pp. 1-4.
Grottick et al., "Studies to investigate the role of 5-HT2c receptors on cocaine- and food-maintained behavior", The Journal of Pharmacology and Experimental Therapeutics, vol. 295 No. 3, 2000, pp. 1183-1191.
Higgins et al., "Serotonin and drug reward: focus on 5-HT2c receptors", European Journal of Pharmacology, 480, 2003, pp. 151-162.
Grauer et al., "WAY-163909, a 5-HT2c agonist, enhances the preclinical potency of current antipsychotics", Psychopharmacology, 2009, 204, pp. 37-48.
Siuciak et al., "CP-809,101, a selective 5-HT2c agonist, shows activity in animal models of antipsychotic activity", Neuropharmacology, 52, 2007, pp. 279-290.
Jenck et al., "The role of 5-HT2c receptors in affective disorders", Expert Opinion on Investigational Drugs, 1998, 7(10), pp. 1587-1600.
Halford, "Obesity drugs in clinical development", Current Opinion in Investigational Drugs, 2006, vol. 7 No. 4, pp. 321-318.
Miller "Serotonin 5-HT2c receptor agonists: potential for the treatment of obesity", Molecular Interventions, Oct. 2005, vol. 5 issue 5, pp. 282-291.
Methvin, "Serotonergic 5-HT2C receptors as a potential therapeutic target for the design antiepileptic drugs", Current Topics in Medicinal Chemistry, 2005, 5, pp. 59-67.
Zhou et al., "Serotonin 2C receptor agonists improve type 2 diabetes via melanocortin-4 receptor signaling pathways", Cell Metab. Nov. 2007 071 6(5), pp. 398-405.
Poste et al., "Lipid vesicles as carriers for introducing biologically active materials into cells", Methods in Cell Biology, vol. XIV, 1976, pp. 33-71.

*Primary Examiner* — Brenda Coleman

(74) *Attorney, Agent, or Firm* — Wood, Phillips, Katz, Clark & Mortimer

(57) ABSTRACT

The present invention generally relates to a series of compounds, to pharmaceutical compositions containing the compounds, and to use of the compounds and compositions as therapeutic agents. More specifically, compounds of the present invention are thienylindole azepines. These compounds are serotonin receptor (5-HT$_{2c}$) ligands and are useful for treating diseases, disorders, and conditions wherein modulation of the activity of serotonin receptors (5-HT$_{2c}$) is desired (e.g. addiction, anxiety, depression, obesity, and others).

9 Claims, No Drawings

THIENYLINDOLE AZEPINES AS SEROTONIN 5-HT$_{2C}$ RECEPTOR LIGANDS AND USES THEREOF

FIELD OF THE INVENTION

The present invention generally relates to a series of compounds, to pharmaceutical compositions containing the compounds, and to use of the compounds and compositions as therapeutic agents. More specifically, compounds of the present invention are thienylindole azepines. These compounds are serotonin receptor (5-HT$_{2C}$) ligands and are useful for treating diseases, disorders, and conditions wherein modulation of the activity of serotonin receptors (5-HT$_{2C}$) is desired (e.g. addiction, anxiety, depression, obesity and others).

BACKGROUND OF THE INVENTION

Serotonin has been implicated in a number of diseases, disorders, and conditions that originate in the central nervous system, including diseases, disorders, and conditions related to, for example, sleeping, eating, perceiving pain, controlling body temperature, controlling blood pressure, depression, anxiety, addiction and schizophrenia. Serotonin also plays an important role in peripheral systems, such as the gastrointestinal system, where it has been found to mediate a variety of contractile, secretory and electrophysiologic effects.

Because of the broad distribution of serotonin within the body, there is a need for drugs that affect serotonergic systems. In particular, agonists, partial agonists, and antagonists of serotonergic systems are of interest for the treatment of a wide range of disorders, including anxiety, depression, hypertension, migraine, obesity, compulsive disorders, schizophrenia, autism, neurodegenerative disorders (e.g., Alzheimer's disease, Parkinsonism and Huntington's chorea), and chemotherapy-induced vomiting.

The major classes of serotonin receptors (5-HT$_{1-7}$) contain one to seven separate receptors that have been formally classified. See Glennon, et al., *Neuroscience and Behavioral Reviews*, 1990, 14, 35; and D. Hoyer, et al. *Pharmacol. Rev.* 1994, 46, 157-203.

For example, the 5-HT$_2$ family of receptors contains 5-HT$_{2a}$, 5-HT$_{2b}$, and 5-HT$_{2c}$ subtypes, which have been grouped together on the basis of primary structure, secondary messenger system, and operational profile. All three 5-HT$_2$ subtypes are G-protein coupled, activate phospholipase C as a principal transduction mechanism, and contain a seven-transmembrane domain structure. There are distinct differences in the distribution of the three 5-HT$_2$ subtypes in a mammal. The 5-HT$_{2b}$ and 5-HT$_{2a}$ receptors are widely distributed in the peripheral nervous system, with 5-HT$_{2a}$ also found in the brain. The 5-HT$_{2c}$ receptor has been found only in the central nervous system, being highly expressed in many regions of the human brain. See G. Baxter, et al. *Trends in Pharmacol. Sci.* 1995, 16, 105-110.

Subtype 5-HT$_{2a}$ has been associated with effects including vasoconstriction, platelet aggregation, and bronchoconstriction, as well as certain CNS effects, while subtype 5-HT$_{2c}$ has been associated with diseases that include depression, anxiety, obsessive compulsive disorder, addiction, panic disorders, phobias, psychiatric syndromes, and obesity. Very little is known about the pharmocologic role of the 5-HT$_{2b}$ receptor. See F. Jenck, et al., *Exp. Opin. Invest. Drugs,* 1998, 7, 1587-1599; M. Bos, et al., *J. Med. Chem.,* 1997, 40, 2762-2769; J. R. Martin, et al., *The Journal of Pharmacology and Experimental Therapeutics,* 1998, 286, 913-924; S. M. Bromidge, et al., 1. *Med. Chem.,* 1998, 41, 1598-1612; G. A. Kennett, *Drugs,* 1998, 1, 4, 456-470; and A. Dekeyne, et al., *Neuropharmacology,* 1999, 38, 415-423.

WO 93/13105, U.S. Pat. Nos. 5,691,330 and 5,532,240 disclose thiophene derivatives; U.S. Pat. No. 4,414,225 discloses thiophene, furan and pyrrole derivatives; U.S. Pat. No. 4,575,504 discloses thienothiazole derivatives; U.S. Pat. No. 5,258,378 discloses certain pyrroloazepine compounds; U.S. Pat. Nos. 4,414,225 and 4,904,653 disclose certain azepine derivatives; WO 2005/019179 discloses certain benzazepines, WO 2005/003096, WO 2005/042490, and WO 2005/042491 disclose benzazepine derivatives; WO 96/11201 discloses furan derivatives; WO 2005/040169 discloses certain fused pyrrole- and pyrazole-containing heterocyclic compounds which are serotonin modulators; WO 2004/024065 discloses substituted bicyclic thiophene derivatives. None of these patents or patent applications disclose compounds of the instant invention.

SUMMARY OF THE INVENTION

The present invention is directed to compounds of the formula:

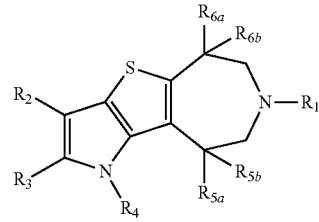

where

R$_1$ is selected from the group consisting of H, alkyl, perhaloalkyl, alkanoyl, C$_{1-8}$ alkylaryl, and C$_{1-8}$ alkylheteroaryl;

R$_2$ and R$_3$ are independently selected from the group consisting of H, halogen, C$_{1-8}$ alkyl, C$_{2-8}$ alkenyl, C$_{2-8}$ alkynyl, perhalo alkyl, CN, OR$_8$, NR$_7$R$_8$, SR$_7$, OCOR$_9$, CONR$_7$R$_8$, NR$_7$COR$_9$, NR$_7$CO$_2$R$_9$, SO$_2$NR$_7$R$_8$, SO$_2$R$_9$, NR$_7$SO$_2$R$_9$, aryl, heteroaryl, C$_{1-8}$ alkylaryl, and C$_{1-8}$ alkylheteroaryl;

R$_4$ is selected from the group consisting of H, C$_{1-8}$ alkyl, C$_{2-8}$ alkenyl, C$_{2-8}$ alkynyl, perhaloalkyl, CONR$_7$R$_8$, COR$_9$, SO$_2$R$_9$, aryl, heteroaryl, C$_{1-8}$ alkylaryl, and C$_{1-8}$ alkylheteroaryl;

R$_{5a}$ and R$_{5b}$ are independently selected from the group consisting of H, C$_{1-8}$alkyl, OR$_7$, aryl, and heteroaryl; or R$_{5a}$ and R$_{5b}$ taken together are —CH$_2$CH$_2$—;

R$_{6a}$ and R$_{6b}$ are independently selected from the group consisting of H, C$_{1-8}$alkyl, OR$_7$, aryl, and heteroaryl; or R$_{6a}$ and R$_{6b}$ taken together are —CH$_2$CH$_2$—;

R$_7$ is selected from the group consisting of H, C$_{1-8}$alkyl, C$_{2-8}$ alkenyl, C$_{2-8}$ alkynyl, perhaloalkyl (preferably CF$_3$), C$_{1-8}$ alkyl-O—C$_{1-8}$ alkyl, aryl, heteroaryl, C$_{1-8}$ alkyl-O-aryl, C$_{1-8}$ alkyl-O-heteroaryl, C$_{1-8}$ alkylaryl, and C$_{1-8}$ alkylheteroaryl;

R$_8$ is selected from the group consisting of H, C$_{1-8}$alkyl, C$_{2-8}$ alkenyl, C$_{2-8}$ alkynyl, perhaloalkyl (preferably CF$_3$), C$_{1-8}$ alkyl-O—C$_{1-8}$ alkyl, aryl, heteroaryl, C$_{1-8}$ alkyl-O-aryl, C$_{1-8}$ alkyl-O-heteroaryl, C$_{1-8}$ alkylaryl, and C$_{1-8}$ alkylheteroaryl; and R$_9$ is selected from the group consisting of C$_{1-8}$ alkyl, C$_{2-8}$ alkenyl, C$_{2-8}$ alkynyl, perhaloalkyl (preferably CF$_3$), C$_{1-8}$ alkyl-O—$C_{1-8}$ alkyl, aryl, heteroaryl, $C_{1-8}$ alkyl-O-aryl, $C_{1-8}$ alkyl-O-heteroaryl, $C_{1-8}$ alkylaryl, and $C_{1-8}$ alkylheteroaryl.

In a preferred embodiment, $R_1$ is H.

In another preferred embodiment, $R_1$ is alkanoyl.

In one preferred embodiment, $R_1$, $R_2$, $R_3$, $R_{5a}$, $R_{5b}$, $R_{6a}$ and $R_{6b}$ are all H, and $R_4$ is selected from the group consisting of H, $C_{1-8}$ alkyl, $C_{2-8}$ alkenyl, $C_{2-8}$ alkynyl, perhaloalkyl, aryl, heteroaryl, $C_{1-8}$ alkylaryl, and $C_{1-8}$ alkylheteroaryl.

In one embodiment, $R_4$ is selected from the group consisting of H, $C_{1-8}$ alkyl, $C_{2-8}$ alkenyl, $C_{2-8}$ alkynyl, perhaloalkyl, aryl, heteroaryl, $C_{1-8}$ alkylaryl, and $C_{1-8}$ alkylheteroaryl, and further wherein said aryl and/or $C_{1-8}$ alkylaryl are substituted with one to three of the substituents selected from the group consisting of H, halo, CN, $NO_2$, $CF_3$, $N_3$, $C_{1-6}$ alkyl, OH, $NR_7R_8$, $OC_{1-6}$ alkyl, $OR_7$, $C(=O)NR_7R_8$, $C(=S)N_7R_8$, tetrazoyl, triazoyl, amidinyl, guanidinyl, thioguanidinyl, cyanoguanadinyl, and aryl.

In another embodiment, $R_4$ is selected from the group consisting of H, $C_{1-8}$ alkyl, $C_{2-8}$ alkenyl, $C_{2-8}$ alkynyl, perhaloalkyl, aryl, heteroaryl, $C_{1-8}$ alkylaryl, and $C_{1-8}$ alkylheteroaryl, and further wherein said heteroaryl and/or $C_{1-8}$ alkylheteroaryl are substituted with one to three of the substituents selected from the group consisting of H, halo, CN, $NO_2$, $CF_3$, $N_3$, $C_{1-6}$ alkyl, OH, $NR_7R_8$, $OC_{1-6}$ alkyl, $OR_7$, $C(=O)NR_7R_8$, $C(=S)N_7R_8$, tetrazoyl, triazoyl, amidinyl, guanidinyl, thioguanidinyl, cyanoguanadinyl, and aryl.

Preferred compounds of the invention include:
1,2,3,6,7,8,9,10-octahydro-8-aza-cyclohepta[e]indene;
3-Ethyl-3,4,5,6,7,8-hexahydro-9-thia-3,6-diaza-cyclopenta[a]azulene;
3-Phenyl-3,4,5,6,7,8-hexahydro-9-thia-3,6-diaza-cyclopenta[a]azulene;
3-Benzyl-3,4,5,6,7,8-hexahydro-9-thia-3,6-diaza-cyclopenta[a]azulene;
3-(4-Chloro-phenyl)-3,4,5,6,7,8-hexahydro-9-thia-3,6-diaza-cyclopenta[a]azulene;
3-(2-Methyl-benzyl)-3,4,5,6,7,8-hexahydro-9-thia-3,6-diaza-cyclopenta[a]azulene;
3-(3-Methyl-benzyl)-3,4,5,6,7,8-hexahydro-9-thia-3,6-diaza-cyclopenta[a]azulene;
3-(4-Methyl-benzyl)-3,4,5,6,7,8-hexahydro-9-thia-3,6-diaza-cyclopenta[a]azulene;
3-Naphthalen-2-ylmethyl-3,4,5,6,7,8-hexahydro-9-thia-3,6-diaza-cyclopenta[a]azulene;
3-(2-Chloro-benzyl)-3,4,5,6,7,8-hexahydro-9-thia-3,6-diaza-cyclopenta[a]azulene;
3-(3-Chloro-benzyl)-3,4,5,6,7,8-hexahydro-9-thia-3,6-diaza-cyclopenta[a]azulene;
3-(4-Chloro-benzyl)-3,4,5,6,7,8-hexahydro-9-thia-3,6-diaza-cyclopenta[a]azulene;
3-p-Tolyl-3,4,5,6,7,8-hexahydro-9-thia-3,6-diaza-cyclopenta[a]azulene;
3-(4-Methoxy-phenyl)-3,4,5,6,7,8-hexahydro-9-thia-3,6-diaza-cyclopenta[a]azulene;
3-m-Tolyl-3,4,5,6,7,8-hexahydro-9-thia-3,6-diaza-cyclopenta[a]azulene;
3-(3-Methoxy-phenyl)-3,4,5,6,7,8-hexahydro-9-thia-3,6-diaza-cyclopenta[a]azulene;
3-(3-Chloro-phenyl)-3,4,5,6,7,8-hexahydro-9-thia-3,6-diaza-cyclopenta[a]azulene;
3-(3-Methoxy-benzyl)-3,4,5,6,7,8-hexahydro-9-thia-3,6-diaza-cyclopenta[a]azulene;
3-(4-Methoxy-benzyl)-3,4,5,6,7,8-hexahydro-9-thia-3,6-diaza-cyclopenta[a]azulene;
3-Cyclohexylmethyl-3,4,5,6,7,8-hexahydro-9-thia-3,6-diaza-cyclopenta[a]azulene;
3-Naphthalen-1-ylmethyl-3,4,5,6,7,8-hexahydro-9-thia-3,6-diaza-cyclopenta[a]azulene;
3-(2,3-Dichloro-benzyl)-3,4,5,6,7,8-hexahydro-9-thia-3,6-diaza-cyclopenta[a]azulene;
3-(3,4-Dichloro-benzyl)-3,4,5,6,7,8-hexahydro-9-thia-3,6-diaza-cyclopenta[a]azulene;
3-Quinolin-8-ylmethyl-3,4,5,6,7,8-hexahydro-9-thia-3,6-diaza-cyclopenta[a]azulene;
3-Isoquinolin-5-ylmethyl-3,4,5,6,7,8-hexahydro-9-thia-3,6-diaza-cyclopenta[a]azulene; and
3-Isoquinolin-1-ylmethyl-3,4,5,6,7,8-hexahydro-9-thia-3,6-diaza-cyclopenta[a]azulene.

The invention also encompasses pharmaceutically acceptable salts of the provided compounds.

Another embodiment of the present invention provides a pharmaceutical composition comprising a compound of the present invention, or a pharmaceutically acceptable salt thereof, and a pharmaceutically acceptable carrier.

Still another embodiment of the present invention provides a method of treating a disease, disorder and/or condition in a mammal (e.g., animal or human), wherein a 5-$HT_{2c}$ receptor is implicated and modulation of a 5-$HT_{2c}$ function is desired. The method comprises administering a therapeutically effective amount of a compound of the present invention, or a pharmaceutically acceptable salt thereof, to the mammal Yet another embodiment of the present invention comprises a method of modulating 5-HT receptor function with an effective amount of compound of the present invention, or a pharmaceutically acceptable salt thereof.

A further embodiment of the present invention provides a method of treating or preventing diseases, disorders, and/or conditions of the central nervous system. The method comprises administering a therapeutically effective amount of a compound of the present invention, or a pharmaceutically acceptable salt thereof, to the mammal.

In a preferred embodiment, the invention provides methods of treating and/or prevention of the following diseases, disorders and/or conditions in a mammal: obesity, psychiatric disorders (including but not limited to depression, schizophrenia, phobias, anxiety, panic disorders, obsessive compulsive disorder, and impulse control disorder); attention deficit disorder, addiction, sleep disorders (including but not limited to narcolepsy, sleep apnea, insomnia, disturbed biological and circadian rhythms, and hyper- and hyposomnolence), migraine, Type II diabetes, and epilepsy.

DETAILED DESCRIPTION OF THE INVENTION

The following definitions are used, unless otherwise described:

The term "alkanoyl" has the general formula RCO—, where R represents an alkyl group. The term acyl can also be used to describe this group. The acyl group is usually derived from a carboxylic acid. Therefore, an alkanoyl group will also include acyl moieties derived from amino acids and dipeptides.

The term "alkyl" as used herein, alone or in combination, includes straight chained and branched hydrocarbon groups containing the indicated number of carbon atoms, typically methyl, ethyl, and straight chain and branched propyl and butyl groups. The term "alkyl" also encompasses cycloalkyl, i.e., a cyclic $C_3$-$C_8$ hydrocarbon group, such as cyclopropyl, cyclobutyl, cyclopentyl, and cyclohexyl.

The term "alkenyl" as used herein, alone or in combination, refers to a substituted or unsubstituted straightchain or substituted or unsubstituted branched-chain alkenyl radical containing from 2 to 10 carbon atoms. Examples of such include, but are not limited to, ethenyl, E- and Z-pentenyl, decenyl and the like.

The term "alkynyl" as used herein, alone or in combination, refers to a substituted or unsubstituted straight or substituted or unsubstituted branched chain alkynyl moiety containing from 2 to 10 carbon atoms. Examples of such include, but are not limited to, ethynyl, propynyl, propargyl, butynyl, hexynyl, decynyl and the like.

The term "alkoxy" as used herein, alone or in combination, refers to an alkyl ether moiety, wherein the term "alkyl" is as defined above. Examples of suitable alkyl ether moieties include, but are not limited to, methoxy, ethoxy, n-propoxy, iso-propoxy, n-butoxy, iso-butoxy, secbutoxy, tert-butoxy and the like.

The term "halo" as used herein, alone or in combination, includes fluoro, chloro, bromo, or iodo. Similarly, the term "halogen" is defined herein to include fluorine, chlorine, bromine, and iodine.

The term "amino" as used herein, alone or in combination, alone or in combination, includes the group —$NH_2$ or —$NR_7R_8$.

The term "aryl," as used herein, alone or in combination, is defined herein as a monocyclic or bicyclic aromatic group (e.g., phenyl or naphthyl) that can be unsubstituted or substituted, for example, with one or more, and in particular one to three of the following substituents selected from the group consisting of H, halo, CN, $NO_2$, $CF_3$, $N_3$, $C_{1-6}$ alkyl, OH, $NR_7R_8$, $OC_{1-6}$ alkyl, $OR_7$, $C(=O)NR_7R_8$, $C(=S)N_7R_8$, tetrazoyl, triazoyl, amidinyl, guanidinyl, thioguanidinyl, cyanoguanadinyl, and aryl. Generally, "aryl" denotes a phenyl group, or an ortho-fused bicyclic carbocyclic group having nine to ten ring atoms in which at least one ring is aromatic (e.g. naphthyl or tetrahydronaphthyl). The term "aryl" also is abbreviated in the various chemical structures as "Ar."

The term "carbocyclic" as used herein, alone or in combination, includes any closed ring of carbon atoms, including alicyclic and aromatic structures.

The term "heteroaryl" as used herein, alone or in combination, includes a monocyclic, bicyclic, or tricyclic ring system containing one, two, or three aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfonyl, and alkylsulfonyl. Examples of heteroaryl groups include, but are not limited to, 2H-pyrrolyl, 3H-indolyl, 4H-quinolizinyl, 4H-carbazolyl, acridinyl, benzo[b]thienyl, benzothiazolyl, 1,3-carbolinyl, carbazolyl, chromenyl, cinnaolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, naptho[2,3-b], oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, and xanthenyl. In one embodiment the term "heteroaryl" denotes a monocyclic aromatic ring containing five or six ring atoms containing carbon and 1, 2, 3, or 4 heteroatoms independently selected from the group consisting of non-peroxide oxygen, sulfur, and N(Z) wherein Z is absent or is H, O, $C_{1-4}$alkyl, phenyl or benzyl. In another embodiment heteroaryl denotes an ortho-fused bicyclic heterocycle of about eight to ten ring atoms.

The term "Het" generally represents a heterocyclic group, saturated or partially unsaturated, containing at least one heteroatom selected from the group consisting of oxygen, nitrogen, and sulfur, and optionally substituted with $C_{1-6}$ alkyl or $C(=O)OR_7$. Typically "Het" is a monocyclic, bicyclic, or tricyclic group containing one or more heteroatoms selected from the group consisting of oxygen, nitrogen, and sulfur. A "Het" group also can contain an oxo group (=O) attached to the ring. Nonlimiting examples of Het groups include 1,3-dihydrobenzofuran, 1,3-dioxolane, 1,4-dioxane, 1,4-dithiane, furanyl, imidazolyl, 2H-pyran, 2-pyrazoline, 4H-pyran, chromanyl, imidazolidinyl, imidazolinyl, indolinyl, isochromanyl, isoindolinyl, morpholine, oxazolyl, piperazinyl, piperidine, piperidynyl, pyrazolidine, pyrimidinyl, pyrazolidinyl, pyrazolinyl, pyrrolidine, pyrroline, quinuclidine, and thiomorpholine.

The present invention is directed to compounds of the formula:

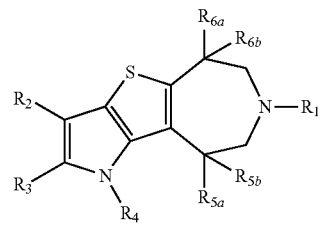

where
$R_1$ is selected from the group consisting of H, alkyl, perhaloalkyl, alkanoyl, $C_{1-8}$ alkylaryl, and $C_{1-8}$ alkylheteroaryl;
$R_2$ and $R_3$ are independently selected from the group consisting of H, halogen, $C_{1-8}$ alkyl, $C_{2-8}$ alkenyl, $C_{2-8}$ alkynyl, perhalo alkyl, CN, $OR_8$, $NR_7R_8$, $SR_7$, $OCOR_9$, $CONR_7R_8$, $NR_7COR_9$, $NR_7CO_2R_9$, $SO_2NR_7R_8$, $SO_2R_9$, $NR_7SO_2R_9$, aryl, heteroaryl, $C_{1-8}$ alkylaryl, and $C_{1-8}$ alkylheteroaryl;
$R_4$ is selected from the group consisting of H, $C_{1-8}$ alkyl, $C_{2-8}$ alkenyl, $C_{2-8}$ alkynyl, perhaloalkyl, $CONR_7R_8$, $COR_9$, $SO_2R_9$, aryl, heteroaryl, $C_{1-8}$ alkylaryl, and $C_{1-8}$ alkylheteroaryl;
$R_{5a}$ and $R_{5b}$ are independently selected from the group consisting of H, $C_{1-8}$alkyl, $OR_7$, aryl, and heteroaryl; or $R_{5a}$ and $R_{5b}$ taken together are —$CH_2CH_2$—;
$R_{6a}$ and $R_{6b}$ are independently selected from the group consisting of H, $C_{1-8}$alkyl, $OR_7$, aryl, and heteroaryl; or $R_{6a}$ and $R_{6b}$ taken together are —$CH_2CH_2$—;
$R_7$ is selected from the group consisting of H, $C_{1-8}$alkyl, $C_{2-8}$ alkenyl, $C_{2-8}$ alkynyl, perhaloalkyl (preferably $CF_3$), $C_{1-8}$ alkyl-O—$C_{1-8}$ alkyl, aryl, heteroaryl, $C_{1-8}$ alkyl-O-aryl, $C_{1-8}$ alkyl-O-heteroaryl, $C_{1-8}$ alkylaryl, and $C_{1-8}$ alkylheteroaryl;
$R_8$ is selected from the group consisting of H, $C_{1-8}$alkyl, $C_{2-8}$ alkenyl, $C_{2-8}$ alkynyl, perhaloalkyl (preferably $CF_3$), $C_{1-8}$ alkyl-O—$C_{1-8}$ alkyl, aryl, heteroaryl, $C_{1-8}$ alkyl-O-aryl, $C_{1-8}$ alkyl-O-heteroaryl, $C_{1-8}$ alkylaryl, and $C_{1-8}$ alkylheteroaryl; and
$R_9$ is selected from the group consisting of $C_{1-8}$ alkyl, $C_{2-8}$ alkenyl, $C_{2-8}$ alkynyl, perhaloalkyl (preferably $CF_3$), $C_{1-8}$ alkyl-O—$C_{1-8}$ alkyl, aryl, heteroaryl, $C_{1-8}$ alkyl-O-aryl, $C_{1-8}$ alkyl-O-heteroaryl, $C_{1-8}$ alkylaryl, and $C_{1-8}$ alkylheteroaryl.

In a preferred embodiment, $R_1$ is H.
In another preferred embodiment, $R_1$ is alkanoyl.
In one preferred embodiment, $R_1$, $R_2$, $R_3$, $R_{5a}$, $R_{5b}$, $R_{6a}$ and $R_{6b}$ are all H, and $R_4$ is selected from the group consisting of H, $C_{1-8}$ alkyl, $C_{2-8}$ alkenyl, $C_{2-8}$ alkynyl, perhaloalkyl, aryl, heteroaryl, alkylaryl, and $C_{1-8}$ alkylheteroaryl.

In one embodiment, $R_4$ is selected from the group consisting of H, $C_{1-8}$ alkyl, $C_{2-8}$ alkenyl, $C_{2-8}$ alkynyl, perhaloalkyl, aryl, heteroaryl, $C_{1-8}$ alkylaryl, and $C_{1-8}$ alkylheteroaryl, and further wherein said aryl and/or $C_{1-8}$ alkylaryl are substituted with one to three of the substituents selected from the group consisting of H, halo, CN, $NO_2$, $CF_3$, $N_3$, $C_{1-6}$ alkyl, OH, $NR_7R_8$, $OC_{1-6}$ alkyl, $OR_7$, $C(=O)NR_7R_8$, $C(=S)N_7R_8$, tetrazoyl, triazoyl, amidinyl, guanidinyl, thioguanidinyl, cyanoguanadinyl, and aryl.

In another embodiment, $R_4$ is selected from the group consisting of H, $C_{1-8}$ alkyl, $C_{2-8}$ alkenyl, $C_{2-8}$ alkynyl, perhaloalkyl, aryl, heteroaryl, alkylaryl, and $C_{1-8}$ alkylheteroaryl, and further wherein said heteroaryl and/or $C_{1-8}$ alkylheteroaryl are substituted with one to three of the substituents selected from the group consisting of H, halo, CN, $NO_2$, $CF_3$, $N_3$, $C_{1-6}$ alkyl, OH, $NR_7R_8$, $OC_{1-6}$ alkyl, $OR_7$, $C(=O)NR_7R_8$, $C(=S)N_7R_8$, tetrazoyl, triazoyl, amidinyl, guanidinyl, thioguanidinyl, cyanoguanadinyl, and aryl.

Preferred compounds of the invention include:
1,2,3,6,7,8,9,10-octahydro-8-aza-cyclohepta[e]indene;
3-Ethyl-3,4,5,6,7,8-hexahydro-9-thia-3,6-diaza-cyclopenta[a]azulene;
3-Phenyl-3,4,5,6,7,8-hexahydro-9-thia-3,6-diaza-cyclopenta[a]azulene;
3-Benzyl-3,4,5,6,7,8-hexahydro-9-thia-3,6-diaza-cyclopenta[a]azulene;
3-(4-Chloro-phenyl)-3,4,5,6,7,8-hexahydro-9-thia-3,6-diaza-cyclopenta[a]azulene;
3-(2-Methyl-benzyl)-3,4,5,6,7,8-hexahydro-9-thia-3,6-diaza-cyclopenta[a]azulene;
3-(3-Methyl-benzyl)-3,4,5,6,7,8-hexahydro-9-thia-3,6-diaza-cyclopenta[a]azulene;
3-(4-Methyl-benzyl)-3,4,5,6,7,8-hexahydro-9-thia-3,6-diaza-cyclopenta[a]azulene;
3-Naphthalen-2-ylmethyl-3,4,5,6,7,8-hexahydro-9-thia-3,6-diaza-cyclopenta[a]azulene;
3-(2-Chloro-benzyl)-3,4,5,6,7,8-hexahydro-9-thia-3,6-diaza-cyclopenta[a]azulene;
3-(3-Chloro-benzyl)-3,4,5,6,7,8-hexahydro-9-thia-3,6-diaza-cyclopenta[a]azulene;
3-(4-Chloro-benzyl)-3,4,5,6,7,8-hexahydro-9-thia-3,6-diaza-cyclopenta[a]azulene;
3-p-Tolyl-3,4,5,6,7,8-hexahydro-9-thia-3,6-diaza-cyclopenta[a]azulene;
3-(4-Methoxy-phenyl)-3,4,5,6,7,8-hexahydro-9-thia-3,6-diaza-cyclopenta[a]azulene;
3-m-Tolyl-3,4,5,6,7,8-hexahydro-9-thia-3,6-diaza-cyclopenta[a]azulene;
3-(3-Methoxy-phenyl)-3,4,5,6,7,8-hexahydro-9-thia-3,6-diaza-cyclopenta[a]azulene;
3-(3-Chloro-phenyl)-3,4,5,6,7,8-hexahydro-9-thia-3,6-diaza-cyclopenta[a]azulene;
3-(3-Methoxy-benzyl)-3,4,5,6,7,8-hexahydro-9-thia-3,6-diaza-cyclopenta[a]azulene;
3-(4-Methoxy-benzyl)-3,4,5,6,7,8-hexahydro-9-thia-3,6-diaza-cyclopenta[a]azulene;
3-Cyclohexylmethyl-3,4,5,6,7,8-hexahydro-9-thia-3,6-diaza-cyclopenta[a]azulene;
3-Naphthalen-1-ylmethyl-3,4,5,6,7,8-hexahydro-9-thia-3,6-diaza-cyclopenta[a]azulene;
3-(2,3-Dichloro-benzyl)-3,4,5,6,7,8-hexahydro-9-thia-3,6-diaza-cyclopenta[a]azulene;
3-(3,4-Dichloro-benzyl)-3,4,5,6,7,8-hexahydro-9-thia-3,6-diaza-cyclopenta[a]azulene;
3-Quinolin-8-ylmethyl-3,4,5,6,7,8-hexahydro-9-thia-3,6-diaza-cyclopenta[a]azulene;
3-Isoquinolin-5-ylmethyl-3,4,5,6,7,8-hexahydro-9-thia-3,6-diaza-cyclopenta[a]azulene; and
3-Isoquinolin-1-ylmethyl-3,4,5,6,7,8-hexahydro-9-thia-3,6-diaza-cyclopenta[a]azulene.

Certain compounds of the invention may exist in different isomeric (e.g. enantiomers and distereoisomers) forms. The invention contemplates all such isomers both in pure form and in admixture, including racemic mixtures. Enol forms are also included.

The compounds of the invention can exist in unsolvated as well as solvated forms, including hydrated forms, e.g., hemihydrate. In general, the solvated forms, with pharmaceutically acceptable solvents such as water, ethanol, and the like are equivalent to the unsolvated forms for the purposes of the invention.

Certain compounds of the invention also form pharmaceutically acceptable salts, e.g., acid addition salts. For example, the nitrogen atoms may form salts with acids. Examples of suitable acids for salt formation are hydrochloric, sulfuric, phosphoric, acetic, citric, oxalic, malonic, salicylic, malic, furmaric, succinic, ascorbic, maleic, methanesulfonic and other mineral carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous hydroxide potassium carbonate, ammonia, and sodium bicarbonate. The free base forms differ from their respective salt forms somewhat in certain physical properties, such as solubility in polar solvents, but the acid salts are equivalent to their respective free base forms for purposes of the invention. (See, for example S. M. Berge, et al., "Pharmaceutical Salts," *J. Pharm. Sci.*, 66: 1-19 (1977) which is incorporated herein by reference.

As used herein, the term "composition" is intended to encompass a product comprising the specified ingredients in the specified amounts, as well as any product which results, directly or indirectly, from a combination of the specified ingredients in the specified amounts.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in *J. Pharmaceutical Sciences*, 1977, 66: 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

Dosage forms for topical administration of a ophthalmic compound of this invention include powders, sprays, ointments and inhalants. The active compound is mixed under sterile conditions with a pharmaceutically acceptable carrier and any needed preservatives, buffers or propellants which can be required. Ophthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.0001 to about 1000 mg/kg/day. For purposes of oral administration, more preferable doses can be in the range of from about 0.001 to about 5 mg/kg/day. If desired, the effective daily dose can be divided into multiple doses for purposes of administration; consequently, single dose compositions may contain such amounts or submultiples thereof to make up the daily dose.

The present invention also provides pharmaceutical compositions that comprise compounds of the present invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

In another aspect, the present invention provides a pharmaceutical composition comprising a component of the present invention and a physiologically tolerable diluent. The present invention includes one or more compounds as described above formulated into compositions together with one or more non-toxic physiologically tolerable or acceptable diluents, carriers, adjuvants or vehicles that are collectively referred to herein as diluents, for parenteral injection, for intranasal delivery, for oral administration in solid or liquid form, for rectal or topical administration, among others.

The compositions can also be delivered through a catheter for local delivery at a target site, via an intracoronary stent (a tubular device composed of a fine wire mesh), or via a biodegradable polymer. The compounds may also be complexed to ligands, such as antibodies, for targeted delivery.

Compositions suitable for parenteral injection may comprise physiologically acceptable, sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfumingagents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

The term "pharmaceutically acceptable prodrugs" as used herein represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. Prodrugs of the present invention may be rapidly transformed in vivo to the parent compound of the above formula, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987), hereby incorporated by reference.

Methods of Treatment

In another embodiment, the present invention provides a method of treating a disease, disorder and/or condition in a mammal (e.g., animal or human), wherein a 5-$HT_2$ receptor is implicated and modulation of a 5-$HT_{2c}$ function is desired. The method comprises administering a therapeutically effective amount of a compound of the present invention, or a pharmaceutically acceptable salt thereof, to the mammal for the purposes of treating and/or preventing the disease, disorder and/or condition.

Yet another embodiment of the present invention comprises a method of modulating 5-HT receptor function with an effective amount of compound of the present invention, or a pharmaceutically acceptable salt thereof.

A further embodiment of the present invention provides a method of treating or preventing diseases, disorders, and/or conditions of the central nervous system (CNS). The method comprises administering a therapeutically effective amount of a compound of the present invention, or a pharmaceutically acceptable salt thereof, to the mammal In a preferred embodiment, the invention provides methods of treating and/or prevention of the following diseases, disorders and/or conditions in a mammal: obesity, psychiatric disorders (including but not limited to depression, schizophrenia, phobias, anxiety, panic disorders, obsessive compulsive disorder, and impulse control disorder); attention deficit disorder, addiction, sleep disorders (including but not limited to narcolepsy, sleep apnea, insomnia, disturbed biological and circadian rhythms, and hyper- and hyposomnolence), migraine, Type II diabetes, and epilepsy. It has been previously demonstrated that 5-$HT_{2C}$ receptors are implicated in these diseases.

Specifically, Grottick et al, *Studies to Investigate the Role of 5-$HT_{2C}$ Receptors on Cocaine-and Food-Maintained Behavior*, The Journal of Pharmacology and Experimental Therapeutics, Vol. 295, No. 3, pp. 1183-1191, 2000, demonstrate that activation of 5-$HT_{2C}$ receptor reduces both food- and cocaine-maintained behavior. Grottick et al, p. 1190, first column, last paragraph.

Higgins et al, *Serotonin and drug reward: focus on 5-$HT_{2C}$ receptors*, European Journal of Pharmacology 480 (2003): 151-162 (from hereon, Higgins et al) disclose that 5-$HT_{2C}$ receptors influence reward-related behavior. The authors discuss animal data which showed that 5-$HT_{2C}$ receptor knockout mice had an increased propensity to self-administer intravenous cocaine. Higgins et al, p. 157, second column, second paragraph. They also state that the "5-$HT_{2C}$ receptor may represent a possible therapeutic target for the development of selective agonists as treatments for aspects of drug abuse." *Id.*, p. 158, second column, last paragraph.

Grauer et al, *WAY-163909, a 5-$HT_{2C}$ agonist, enhances the preclinical potency of current antipsychotics*, Psychopharmacology (2009) 204: 37-48 (from hereon, Grauer et al) teach that 5-$HT_{2C}$ agonists may enhance the potency of antipsychotic medications. Grauer et al, p. 37, Conclusion and p. 45, first column, second full paragraph.

Siuciak et al, *CP-809,101, a selective 5-$HT_{2C}$ agonist, shows activity in animal models of antipsychotic activity*, Neuropharmacology 52 (2007) 279-290 (from hereon, Siuciak et al) teach that 5-$HT_{2C}$ receptor agonists may be used in the treatment of schizophrenia. Siuciak et al, Abstract.

Jason C G Halford, *Obesity drugs in clinical development*, Current Opinion in Investigational Drugs, 2006 7(4): 312-318 (from hereon, Harford) states that serotonin 5-$HT_{2C}$ receptor agonists have been shown to reduce food intake and body weight gain in rodents, and to reduce calorie intake, appetite, and body weight in humans. Halford, p. 313, second column, first full paragraph.

Likewise, Keith Miller, *Serotonin-5$HT_{2C}$ Receptor Agonists: Potential for the Treatment of Obesity*, Molecular Interventions, October 2005, Volume 5, Issue 5, pp. 283-291 (from hereon, Miller) shows that 5-$HT_{2C}$ receptor is a compelling target for the treatment of obesity. Miller, p. 288, Conclusion.

Methyin Isaac, *Serotonergic 5-$HT_{2C}$ Receptors as a Potential Therapeutic Target for the Design Antiepileptic Drugs*, Current Topics in Medicinal Chemistry 2005, 5, 59-67 (from hereon, Isaac) teaches that "[t]he 5-$HT_{2C}$ receptor subtype appears to be a rational target for the development of novel antiepileptic drugs." Isaac, p. 65, second column, second-to-last paragraph.

Martin et al, *5-$HT_{2C}$ Receptor Agonists: Pharmacological Characteristics and Therapeutic Potential*, The Journal of Pharmacology and Experimental Therapeutics, Vol. 286, No. 2, pp. 913-924 (from hereon, Martin et al) conducted several experiments and concluded that certain 5-$HT_{2C}$ receptor agonists demonstrated both their excellent tolerability and their therapeutic potential for obsessive compulsive disorder and depression. Martin et al, p. 923, last paragraph.

Zhou et al, *Serotonin 2C receptor agonists improve type 2 diabetes via melanocortin-4 receptor signaling pathways*, Cell Metab. 2007 November; 6(5) 398-405 (from hereon, Zhou et al) teach that 5-$HT_{2C}$ receptor agonists may improve glucose tolerance and reduce plasma insulin in murine models of obesity and type 2 diabetes. Zhou et al, Abstract.

All of the scientific publications, patent applications and patents cited in this specification are herein incorporated in their entirety by reference.

SCHEMES AND EXAMPLES

The compounds of the present invention may be prepared by the procedures set forth in Scheme 1.

List Of Abbreviations

The following abbreviations are used in Scheme 1 and Examples below.

| Abbreviation | Definition |
| --- | --- |
| Ar | argon |
| $CHCl_3$ | chloroform |
| $Cs_2CO_3$ | cesium carbonate |
| CuI | copper iodide |
| DCM | dichloromethane |
| DMF | dimethylformamide |
| DMSO | dimethylsulfoxide |
| ESI | electrospray ionization |
| $Et_2O$ | diethylether |
| EtOAc | ethyl acetate |
| EtOH | ethanol |
| HCl | hydrochloric acid |
| HPLC | high-performance liquid chromatography |
| KOH | potassium hydroxide |
| MeOH | methanol |
| $MgSO_4$ | magnesium sulfate |
| $Na_2SO_4$ | sodium sulfate |
| NaH | sodium hydride |
| $NaHCO_3$ | sodium bicarbonate |
| $NH_4Cl$ | ammonium chloride |
| $NH_4OAc$ | ammonium acetate |
| $NH_4OH$ | ammonium hydroxide |
| NMP | N-methyl-2-pyrrolidone |
| RT | room temperature |
| TEA | triethylamine |
| THF | tetrahydrofuran |

The general analytical conditions set forth below were utilized in all examples.

General Analytical/Instrumentation Information:
1. Reverse-phase HPLC analysis and purification was performed using a Waters 2525 binary gradient pump, Waters 2767 sample manager, waters 2487 UV detector (220 and 254 nM), Waters reagent manager (for prep runs), and Waters Micromass ZQ electrospray mass spec detector. The Micromass ZQ was set for both positive and negative ionization (cone voltage=25 and 50, respectively). Analytical HPLC analysis was performed as follows:
Waters XTerra MS C18 50×4.6 mm 3.5 µm column
Mobile Phase: 10 mM ammonium acetate buffer in water and methanol
Methanol: 10 to 75% at 3.5 minutes, 75 to 99% at 3.9 minutes, 99% hold to 4.2 minutes, 99 to 10% at 4.5 minutes, re-equilibrate.
Flow rate—2.25 ml/min
Preparative HPLC was performed as follows:
Waters XTerra Prep MS C18 100×19 mm 5 µm column
Mobile Phase: 10 mM ammonium acetate buffer in water and methanol Methanol: 10 to 99% at 16 minutes, 99% hold to 18 minutes, 99 to 10% at 19 minutes, re-equilibrate
Flow rate—24 ml/min
2. NMR analysis was performed using a Bruker BioSpin UltraSheild NMR (300 MHz).
3. Microwave Synthesis: Biotage Initiator
4. Flash silica-gel chromatography: Teledyne Isco CombiFlash $R_f$
5. Parr Hydrogenation Apparatus w/Parr 4833 temperature controller Scheme 1
Synthesis of 3-substituted-3,4,5,6,7,8-hexahydro-9-thia-3,6-diaza-cyclopenta[a]azulene compounds

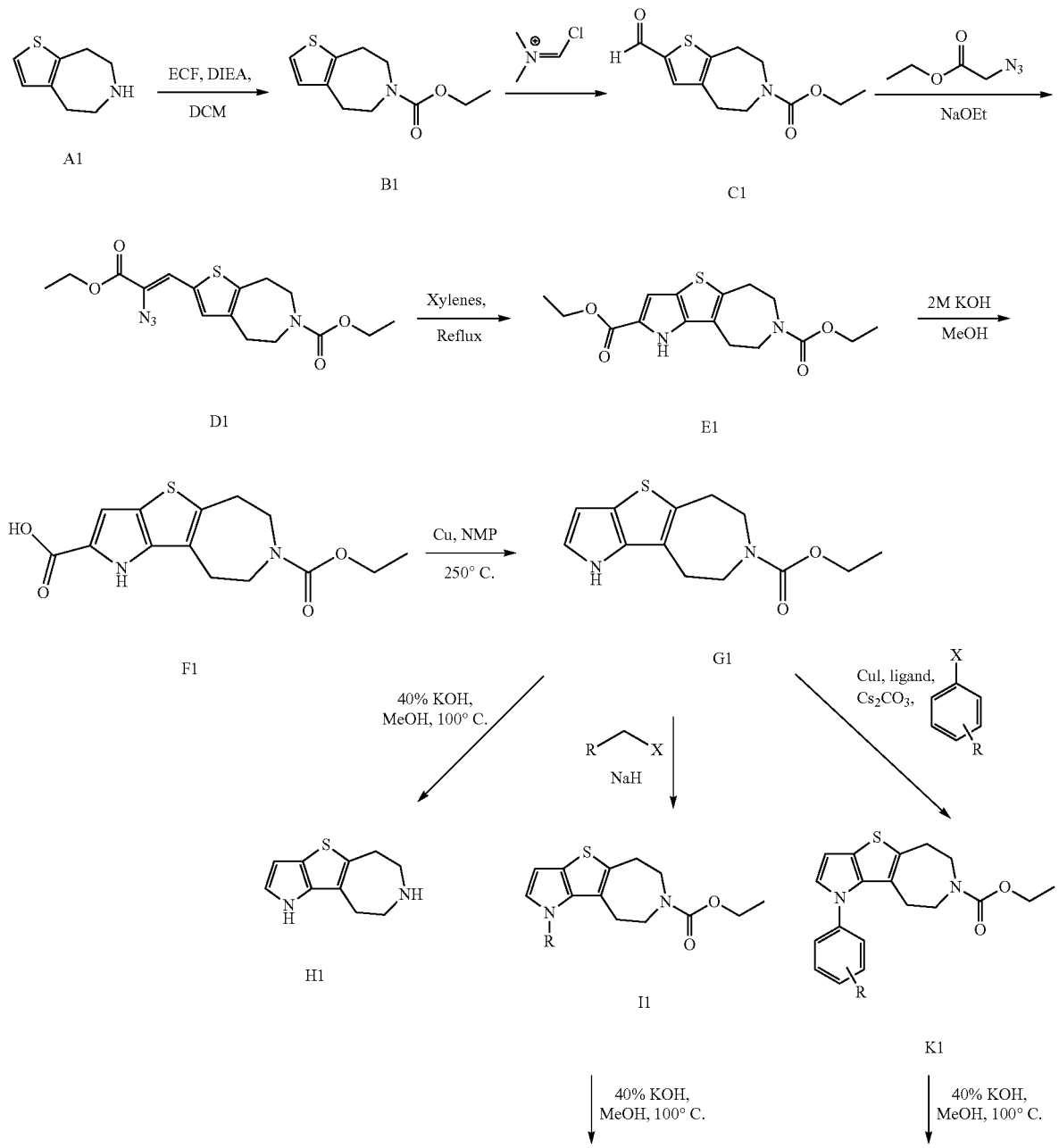

-continued

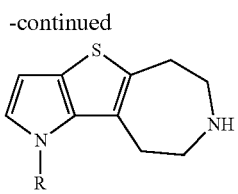

J1

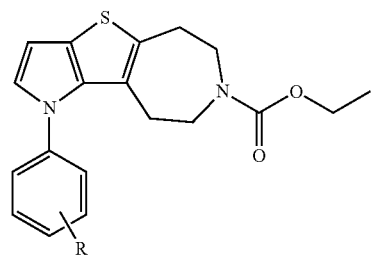

L1

The basic amine of compound A1 can be derivatized with a variety of protecting groups. Protecting group selection was based on several factors including ease/cost of synthesis, compatibility/stability of anticipated chemistries, and ease of removal. Under typical conditions, compound A1 was protected as the ethyl carbamate to give compound B1. In an effort to install the indolic-like ring system on the thiophene scaffold, compound B1 was subjected to Vilsmeier-Haack formylation (*Ber.* 1927, 60, 119) conditions to give aldehyde C1. Condensation of compound C1 with ethyl azidoacetate under basic conditions gave the corresponding adduct D1. Intramolecular cyclization of adduct D1 in refluxing xylene furnished the ester E1. Ester E1 was hydrolysed under standard conditions to give acid F1 that was decarboxylated in the presence of copper in NMP at 250° C. to give key intermediate G1. The pyrrolic-nitrogen of compound G1 may substituted by a variety of synthetic procedures. Treatment of compound G1 with a strong base like sodium hydride and alkylating agents such as alkyl halides gave compounds of the general structure H. Alternatively, compound G1 can be treated under "Ullmann-type" conditions to give aryl-substituted analogs of general structure K1. Deprotection of compounds G1, H, and K1 can be accomplished by a variety of conditions including TMSI, 33% HBr/acetic acid, and 40% KOH/methanol, to name a few. The latter of which was chosen as the preferred method for these particular compounds because of its higher yield.

The following examples are illustrative of the preparation of representative compounds of the present invention. They are not meant to limit the invention in any way.

Example 1.

3,4,5,6,7,8-Hexahydro-9-thia-3,6-diaza-cyclopenta[a]alazulene

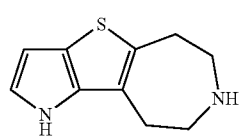 [SMILES: c1cc2sc3c(c2[nH]1)CCNCC3]

a) 5,6,7,8-Tetrahydro-4H-thieno[2,3-d]azepine

The subtitled compound was prepared by a method described previously by Frehel et al. [J, Heterocyclic Chem., 22, 1011 (1985)] to give 5,6,7,8-tetrahydro-4H-thieno[2,3-d]azepine as a yellow oil. A small portion of 5,6,7,8-tetrahydro-4H-thieno[2,3-d]azepine was purified by HPLC. In general, this material was carried on without further purification. $^1$H NMR (300 MHz, DMSO) 7.20 (d, J=5 Hz, 1 H), 6.85 (d, J=5 Hz, 1 H), 3.42-3.61 (m, 4 H), 2.71-3.03 (m, 4 H); MS: ESI (positive): 154 (M+H).

b) 4,5,7,8-Tetrahydro-thieno[2,3-d]azepine-6-carboxylic acid ethyl ester

To a solution of 5,6,7,8-tetrahydro-4H-thieno[2,3-d]azepine (951 mg, 5.03 mmol) in THF (20 ml) at 0° C. was added triethylamine (1526 mg, 15.09 mmol) and ethyl chloroformate (573 mg, 5.3 mmol). The reaction mixture was warmed to ambient temperature for 4 hours and then diluted with water (100 ml) and extracted with EtOAc (3×75 ml). The combined organic phases were washed with brine (100 ml), dried (MgSO$_4$), and concentrated in vacuo to give the crude product as an oil. Purification by flash chromatography (gradient elution: 0 to 40% EtOAc in hexane) afforded the subtitled compound as an oil; yield 77%. $^1$H NMR (300 MHz, CDCl$_3$) 6.96 (d, J=5 Hz, 1 H), 6.76 (d, J=5 Hz, 1 H), 4.18 (q, J=7 Hz, 2 H), 3.52-3.78 (m, 4 H), 2.78-3.08 (m, 4 H), 1.28 (t, J=7 Hz, 3 H); MS: ESI (positive): 226 (M+H).

c) 2-Formyl-4,5,7,8-tetrahydro-thieno[2,3-d]azepine-6-carboxylic acid ethyl ester To a stirred solution of 4,5,7,8-tetrahydro-thieno[2,3-d]azepine-6-carboxylic acid ethyl ester (1.50 g, 6.65 mmol) in 1,2-dichloroethane (20 ml) was added Vilsmeier reagent (1.49 g, 11.65 mmol). The reaction mixture was heated to 70° C. for 5 hours. The reaction mixture was allowed to cool to RT followed by addition of 1 M sodium acetate (20 ml). The mixture was vigorously stirred for 2 hours and then diluted with water (50 ml). The resulting solution was extracted with DCM (3×). The combined DCM extracts were washed with water, brine, and dried over MgSO$_4$. The resulting mixture was filtered and solvent evaporated in vacuo to give the subtitled compound as a tan oil (1.56 g) that was used without further purification. MS: ESI (positive): 254 (M+H).

d) 2-(2-Azido-2-ethoxycarbonyl-vinyl)-4,5,7,8-tetrahydro-thieno[2,3-d]azepine-6-carboxylic acid ethyl ester A solution of sodium ethoxide in ethanol (21 wt % in EtOH, 8 ml, 21.4 mmol) was diluted with additional ethanol (~5 ml) and cooled to 0° C. To this solution was added the product from step (c) (4.50 g, 17.76 mmol) and ethyl azidoacetate (25% wt % in EtOH, 11 ml, 21.4 mmol). The reaction mixture was stirred and allowed to warm to RT over 16 hrs. The reaction mixture was then quenched by pouring into saturated aqueous NH$_4$Cl. The aqueous mixture was extracted with Et$_2$O (3×). The combined Et$_2$O extracts were washed with brine, dried (MgSO$_4$), filtered, and solvent evaporated in vacuo to give an orange oil. The crude oil was purified by flash silica-gel chromatography (gradient elution: 0 to 45% EtOAc in hexanes) to give the subtitled compound as a yellow oil (2.9 g). MS: ESI (positive): 365 (M+H).

e) 4,5,7,8-Tetrahydro-3H-9-thia-3,6-diaza-cyclopenta[a]azulene-2,6-dicarboxylic acid diethyl ester To a solution of xylenes (35 ml) at 100° C. was added a solution of the product from step (d) (2.90 g, 7.96 mmol) in xylenes (15 ml). The mixture was heated for 1 hour and then allowed to cool to RT. The solvent was evaporated in vacuo to give a yellow solid which was purified via flash silica-gel chromatography (gradient elution: 0 to 75% EtOAc in hexane) to give the subtitled compound as a tan solid (2.4 g). $^1$H NMR (CDCl$_3$) δ 8.92 (bs, 1H), 7.04 (d, J=1.8 Hz, 1 H), 4.36 (q, J=6.9 Hz, 2H), 4.20 (q, J=7.2 Hz, 2H), 3.76-3.62 (m, 4 H), 3.08-2.96 (m, 2 H), 2.96-2.84 (m, 2 H), 1.39 (t, J=7.2 Hz, 3H), 1.30 (t, J=6.9 Hz, 3H); MS: ESI (positive): 337 (M+H).

f) 4,5,7,8-Tetrahydro-3H-9-thia-3,6-diaza-cyclopenta [a]azulene-2,6-dicarboxylic acid 6-ethyl ester To a stirred solution of the product from step (e) (3.45 g, 10.26 mmol) in EtOH (120 ml) was added 2M KOH (50 ml). The reaction mixture was heated to 50° C. for 6 hours and then allowed to cool to RT. The reaction mixture was then stirred at RT for an additional 12 hours. The MeOH was then evaporated in vacuo and the remaining aqueous mixture was diluted with additional water (50 ml). The aqueous mixture was washed with EtOAc (2×). The aqueous mixture was then acidified with 2M HCl to pH 2 and extracted with DCM (3×). The combined DCM extracts were dried (Na$_2$SO$_4$), decanted, and solvent evaporated in vacuo to give the sub-titled compound as a tan solid (3.0 g) that was used without further purification. MS: ESI (positive): 308 (M+H), ESI (negative): 307 (M+H).

g) 4,5,7,8-Tetrahydro-3H-9-thia-3,6-diaza-cyclopenta[a]azulene-6-carboxylic acid ethyl ester To a stirred solution of the product from step (f) (0.50 g, 1.62 mmol) in NMP (10 ml) was added copper dust (0.10 g, 1.62 mmol). The reaction mixture was heated in a microwave reactor to 250° C. for 20 minutes. The cooled solution was diluted with water (100 ml) and extracted with Et$_2$O (3×). The combined Et$_2$O extracts were washed with brine, dried (MgSO$_4$), filtered, and solvent evaporated in vacuo to give the crude product. Purification by silica-gel chromatography (gradient elution: 0 to 100% EtOAc in hexanes gave the sub-titled compound as a tan solid (0.40 g). MS: ESI (positive): 265 (M+H).

h) 3,4,5,6,7,8-Hexahydro-9-thia-3,6-diaza-cyclopenta[a]azulene

To a stirred solution of the product from step (g) (0.049 g, 0.19 mmol) in EtOH (2 ml) was added 40% aqueous KOH (2 ml). The reaction mixture was heated to 100° C. until LCMS indicated no starting material present (usually 16-32 hours). The reaction mixture was cooled to RT, diluted with water (30 ml) and extracted with DCM (3×). The combined DCM extracts were dried (MgSO$_4$), filtered, and solvent evaporated in vacuo to give the crude product. Purification by preparative LCMS gave the title compound as a tan solid. $^1$H NMR (CDCl$_3$) δ 8.05 (bs, 1H), 6.95-6.90 (m, 1 H), 6.41-6.36 (m, 1H), 3.10-3.02 (m, 4H), 3.00-2.94 (m, 2 H), 2.92-2.82 (m, 2 H); MS: ESI (positive): 193 (M+H).

Example 2

3-Ethyl-3,4,5,6,7,8-hexahydro-9-thia-3,6-diaza-cyclopenta[a]azulene

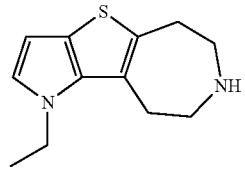

a) 3-Ethyl-4,5,7,8-tetrahydro-3H-9-thia-3,6-diaza-cyclopenta[a]azulene-6-carboxylic acid ethyl ester To a stirred solution of the product of Example 1, step (g) (0.068 g, 0.26 mmol) in DMF (4 ml) at 0° C. under argon was added NaH (60% dispersion by wt., 0.015 g, 0.39 mmol) followed by ethyl bromide (0.029 ml, 0.39 mmol). The reaction mixture was stirred at 0° C. for 2 hrs and then quenched by slow addition of saturated aqueous citric acid (40 ml). The aqueous mixture was extracted with DCM (3×). The combined DCM extracts were washed with water (2×), brine, dried (MgSO$_4$), filtered, and solvent evaporated in vacuo to give the crude product. Purification by silica-gel chromatography (gradient elution: 0 to 50% EtOAc in hexanes) gave the sub-titled compound as a tan solid (0.060 g). $^1$H NMR (CDCl$_3$) δ 6.75 (d, J=3.0 Hz, 1 H), 6.24 (d, J=3.0 Hz, 1H), 4.40-4.08 (m, 4H), 3.96-3.62 (m, 4 H), 3.34-2.92 (m, 4 H), 1.42 (t, J=6.9 Hz, 3 H), 1.28 (t, J=6.9 Hz, 3H); MS: ESI (positive): 293 (M+H).

b) 3-Ethyl-3,4,5,6,7,8-hexahydro-9-thia-3,6-diaza-cyclopenta[a]azulene

To a stirred solution of the product from step (a) (0.060 g, 0.21 mmol) in EtOH (2 ml) was added 40% aqueous KOH (2 ml). The reaction mixture was heated to 100° C. until LCMS indicated that the reaction was complete (usually 16-32 hours). The reaction mixture was cooled to RT, diluted with water (30 ml), and extracted with DCM (3×). The combined DCM extracts were dried (MgSO$_4$), filtered, and solvent evaporated in vacuo to give the crude product. Purification by preparative HPLC gave the title compound as a tan solid. $^1$H NMR (CD$_3$)$_2$CO™ 6.82 (d, J=2.7 Hz, 1H), 6.14 (d, J=2.7 Hz, 1H), 4.20 (q, J=7.2 Hz, 2H), 3.01-2.92 (m, 6H), 2.86-2.78 (m, 2H), 1.35 (t, J=7.2 Hz, 3H); MS: ESI (positive): 221 (M+H).

Example 3

3-Phenyl-3,4,5,6,7,8-hexahydro-9-thia-3,6-diaza-cyclopenta[a]azulene

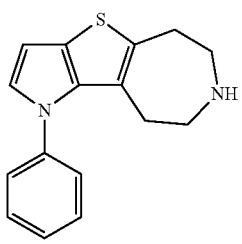 [SMILES: c1ccc(-n2ccc3sc4c(c32)CCNCC4)cc1]

a) 3-Phenyl-4,5,7,8-tetrahydro-3H-9-thia-3,6-diaza-cyclopenta[a]azulene-6-carboxylic acid ethyl ester To a stirred solution of the product of Example 1, step (g) (0.056 g, 0.21 mmol) in dioxane (1.5 ml) under argon was added iodobenzene (0.026 ml, 0.23 mmol), Cs$_2$CO$_3$ (0.15 g, 0.45 mmol), CuI (0.002 g, 0.01 mmol), and (+)-trans-1,2-diaminocyclohexane (0.005 ml, 0.04 mmol). The reaction mixture was heated to 100° C. until LCMS indicated the reaction was complete (usually 16 hours). The reaction mixture was cooled to RT, diluted with DCM, and filtered through celite. The solvent was evaporated in vacuo and the residue purified by flash silica-gel chromatography (gradient elution: 0 to 50% EtOAc in hexanes) to give the sub-titled compound as a colorless oil (0.066 g). $^1$H NMR (CD$_3$OD) δ 7.53-7.39 (m, 3H), 7.38-7.32 (m, 2H), 6.92 (d, J=3.0 Hz, 1H), 6.38 (d, J=3.0 Hz, 1H), 4.18-4.06 (m, 2H), 3.68-3.58 (m, 2H), 3.48-3.42 (m, 2H), 3.00-2.94 (m, 2H), 2.54-2.46 (m, 2H), 1.30-1.16 (m, 3H); MS: ESI (positive): 341 (M+H).

b) 3-Phenyl-3,4,5,6,7,8-hexahydro-9-thia-3,6-diaza-cyclopenta[a]azulene

To a stirred solution of the product from step (a) (0.066 g, 0.19 mmol) in EtOH (2 ml) was added 40% aqueous KOH (2 ml). The reaction mixture was heated to 100° C. until LCMS that the reaction was complete (usually 16-32 hours). The reaction mixture was cooled to RT, diluted with water (30 ml), and extracted with DCM (3×). The combined DCM extracts were dried (MgSO$_4$), filtered, and solvent evaporated in vacuo to give the crude product. Purification by preparative HPLC gave the title compound as a tan solid. $^1$HNMR (CD$_3$)$_2$CO™ 7.52-7.50 (m, 2H), 7.44-7.41 (m, 3H), 6.97 (d, J=3 Hz, 1H), 6.42 (d, J=3 Hz, 1H), 2.92-2.89 (m, 4H), 2.74-2.71 (m, 2H), 2.52-2.49 (m, 2H), 2.06-2.04 (m, 1H); MS: ESI (positive): 269 (M+H).

Example 4

3-Benzyl-3,4,5,6,7,8-hexahydro-9-thia-3,6-diaza-cyclopenta[a]azulene

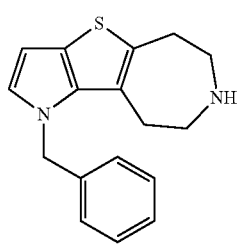 [SMILES: c1ccc(Cn2ccc3sc4c(c32)CCNCC4)cc1]

Example 4 was prepared in a similar fashion to Example 2 except benzyl bromide was used instead of ethyl bromide (Example 2, step (a)). $^1$H NMR (CD$_3$)$_2$CO δ 7.96-7.80 (m, 3H), 7.69-7.50 (m, 3H), 6.87 (s, 1H), 6.0 (s, 2H), 3.49-3.13 (m, 8H); MS: ESI (positive): 283 (M+H).

Example 5

3-(4-Chloro-phenyl)-3,4,5,6,7,8-hexahydro-9-thia-3,6-diaza-cyclopenta[a]azulene

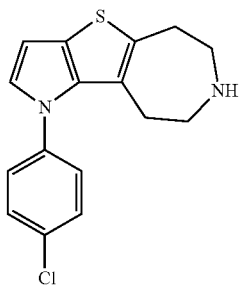 [SMILES: Clc1ccc(-n2ccc3sc4c(c32)CCNCC4)cc1]

Example 5 was prepared in a similar fashion to Example 3 except 1-chloro-4-iodobenzene was used instead of iodobenzene (Example 3, step (a)). Product recovered as acetate salt from preparative HPLC. $^1$HNMR (CDCl$_3$) δ 8.57 (s, 2H), 7.44-7.42 (m, 2H), 7.30-7.26 (m, 2H), 6.87 (d, J=3 Hz, 1H), 6.46 (d, J=3 Hz, 1H), 3.24-3.20 (m, 2H), 3.16-3.12 (m, 2H), 3.04-3.01 (m, 2H), 2.75-2.72 (m, 2H), 1.94 (s, 3H); MS: ESI (positive): 303 (M+H).

Example 6

3-(2-Methyl-benzyl)-3,4,5,6,7,8-hexahydro-9-thia-3,6-diaza-cyclopenta[a]azulene

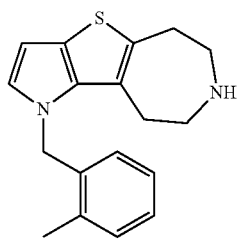 [SMILES: Cc1ccccc1Cn1ccc2sc3c(c21)CCNCC3]

Example 6 was prepared in a similar fashion to Example 2 except 2-methyl-benzyl bromide was used instead of ethyl bromide (Example 2, step (a)). Product recovered as acetate salt from preparative HPLC. $^1$HNMR (CDCl$_3$) δ 7.18-7.17 (m, 2H), 7.09-7.05 (m, 1H), 6.75 (d, J=2.7 Hz, 1H), 6.48 (d, J=7.5 Hz, 1H), 6.34 (d, J=3 Hz, 1H), 5.24 (s, 2H), 4.88 (s, 2H), 3.15-3.04 (m, 4H), 2.80 (s, 4H), 2.32 (s, 3H), 1.93 (s, 3H); MS: ESI (positive): 297 (M+H).

Example 7

3-(3-Methyl-benzyl)-3,4,5,6,7,8-hexahydro-9-thia-3,6-diaza-cyclopenta[a]azulene

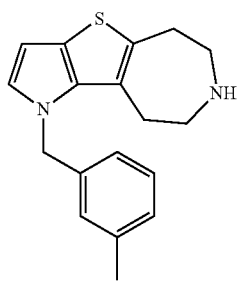 [SMILES: Cc1cccc(Cn2ccc3sc4c(c32)CCNCC4)c1]

Example 7 was prepared in a similar fashion to Example 2 except 3-methyl-benzyl bromide was used instead of ethyl bromide (Example 2, step (a)). Product recovered as acetate salt from preparative HPLC. $^1$HNMR (CDCl$_3$) δ 7.17 (t, J=7.5 Hz, 1H), 7.07 (m, 1H), 6.83-6.70 (m, 5H), 6.34 (d, J=3 Hz, 1H), 5.27 (s, 2H), 3.17-3.13 (m, 2H), 3.09-3.05 (m, 2H), 2.95-2.92 (m, 2H), 2.85-2.82 (m, 2H), 2.29 (s, 3H), 1.92 (s, 3H); MS: ESI (positive): 297 (M+H).

Example 8

3-(4-Methyl-benzyl)-3,4,5,6,7,8-hexahydro-9-thia-3,6-diaza-cyclopenta[a]azulene

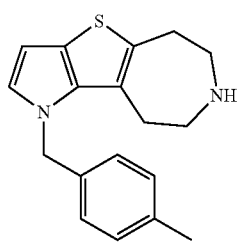 [SMILES: Cc1ccc(Cn2ccc3sc4c(c32)CCNCC4)cc1]

Example 8 was prepared in a similar fashion to Example 2 except 4-methyl-benzyl bromide was used instead of ethyl bromide (Example 2, step (a)). Product recovered as acetate salt from preparative HPLC. $^1$HNMR (CDCl$_3$) δ 7.09 (d, J=8.1 Hz, 2H), 6.86-6.81 (m, 3H), 6.33 (d, J=3 Hz, 1H), 5.39-5.27 (m, 4H), 3.13-3.10 (m, 2H); 3.05-3.02 (m, 2H), 2.91-2.88 (m, 2H), 2.83-2.80 (m, 2H), 2.31 (s, 3H), 1.92 (s, 3H); MS: ESI (positive): 297 (M+H).

Example 9

3-Naphthalen-2-ylmethyl-3,4,5,6,7,8-hexahydro-9-thia-3,6-diaza-cyclopenta[a]azulene

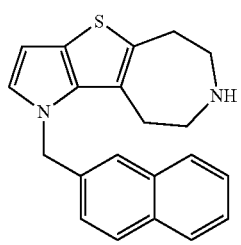 [SMILES: c1ccc2cc(Cn3ccc4sc5c(c43)CCNCC5)ccc2c1]

Example 9 was prepared in a similar fashion to Example 2 except 2-(bromomethyl)naphthalene was used instead of ethyl bromide (Example 2, step (a)). Product recovered as acetate salt from preparative HPLC. $^1$HNMR (CDCl$_3$) δ 7.80-7.77 (m, 2H), 7.75-7.69 (m, 1H), 7.47-7.44 (m, 2H), 7.36 (s, 1H), 7.14-7.10 (m, 1H), 6.90 (d, J=3 Hz, 1H), 6.39 (d, J=2.7 Hz, 1H), 6.10 (s, 2H), 5.46 (s, 2H), 3.12-3.10 (m, 2H), 3.06-

3.04 (m, 2H), 2.95-2.92 (m, 2H), 2.79-2.75 (m, 2H), 1.86 (s, 3H); MS: ESI (positive): 333 (M+H).

Example 10

3-(2-Chloro-benzyl)-3,4,5,6,7,8-hexahydro-9-thia-3,6-diaza-cyclopenta[a]azulene

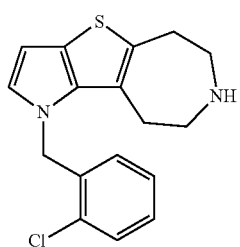 [SMILES: Clc1ccccc1Cn1ccc2sc3c(c21)CCNCC3]

Example 10 was prepared in a similar fashion to Example 2 except 2-chloro-benzyl bromide was used instead of ethyl bromide (Example 2, step (a)). Product recovered as acetate salt from preparative HPLC. $^1$HNMR (CDCl$_3$) δ 7.41-7.38 (m, 1H), 7.24-7.10 (m, 2H), 6.83 (d, J=3 Hz, 1H), 6.63 (m, 2H), 6.45 (d, J=7.8 Hz, 1H), 6.37 (d, J=3 Hz, 1H), 5.36 (s, 2H), 3.17-3.06 (m, 4H), 2.83-2.80 (m, 4H), 1.92 (s, 3H); MS: ESI (positive): 317 (M+H).

Example 11

3-(3-Chloro-benzyl)-3,4,5,6,7,8-hexahydro-9-thia-3,6-diaza-cyclopenta[a]azulene

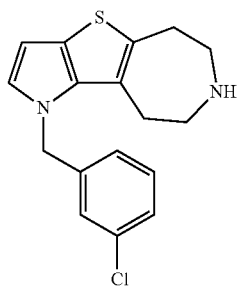 [SMILES: Clc1cccc(Cn2ccc3sc4c(c32)CCNCC4)c1]

Example 11 was prepared in a similar fashion to Example 2 except 3-chloro-benzyl bromide was used instead of ethyl bromide (Example 2, step (a)). Product recovered as acetate salt from preparative HPLC. $^1$HNMR (CDCl$_3$) δ 7.26-7.22 (m, 2H), 6.99 (s, 1H), 6.82-6.81 (m, 2H), 6.36 (d, J=2.7 Hz, 1H), 5.93 (bs, 2H), 5.28 (s, 2H), 3.17-3.14 (m, 2H), 3.09-3.05 (m, 2H), 2.89 (bs, 2H), 1.94 (s, 3H); MS: ESI (positive): 317 (M+H).

Example 12

3-(4-Chloro-benzyl)-3,4,5,6,7,8-hexahydro-9-thia-3,6-diaza-cyclopenta[a]azulene

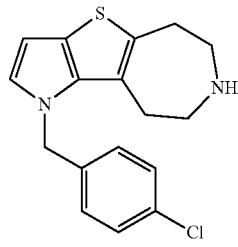 [SMILES: Clc1ccc(Cn2ccc3sc4c(c32)CCNCC4)cc1]

Example 12 was prepared in a similar fashion to Example 2 except 4-chloro-benzyl bromide was used instead of ethyl bromide (Example 2, step (a)). Product recovered as acetate salt from preparative HPLC. $^1$HNMR (CDCl$_3$) δ 7.28-7.25 (m, 2H), 6.88 (d, J=8.4 Hz, 2H), 6.82 (d, J=3 Hz, 1H), 6.53 (br. s, 2H), 6.35 (d, J=3 Hz, 1H), 5.28 (s, 2H), 3.17-3.14 (m, 2H), 3.08-3.05 (m, 2H), 2.88 (s, 4H), 1.93 (s, 3H); MS: ESI (positive): 317 (M+H).

Example 13

3-p-Tolyl-3,4,5,6,7,8-hexahydro-9-thia-3,6-diaza-cyclopenta[a]azulene

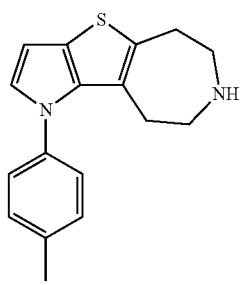 [SMILES: Cc1ccc(-n2ccc3sc4c(c32)CCNCC4)cc1]

Example 13 was prepared in a similar fashion to Example 3 except 4-iodotoluene was used instead of iodobenzene (Example 3, step (a)). Product recovered as acetate salt from preparative HPLC. $^1$HNMR (CDCl$_3$) δ 9.18 (s, 2H), 7.26-7.20 (4H), 6.88 (d, J=3 Hz, 1H), 6.43 (d, J=3 Hz, 1H), 3.26-

3.22 (m, 2H), 3.17-3.13 (m, 2H), 3.05-3.02 (m, 2H), 2.76-2.72 (m, 2H), 2.42 (s, 3H), 1.94 (s, 3H); MS: ESI (positive): 283 (M+H).

Example 14

3-(4-Methoxy-phenyl)-3,4,5,6,7,8-hexahydro-9-thia-3,6-diaza-cyclopenta[a]azulene

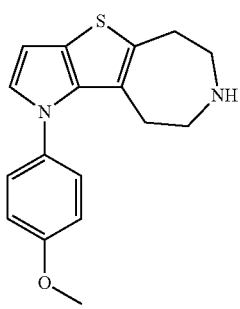 [SMILES: COc1ccc(-n2ccc3sc4c(c32)CCNCC4)cc1]

Example 14 was prepared in a similar fashion to Example 3 except 4-iodoanisole was used instead of iodobenzene (Example 3, step (a)). Product recovered as acetate salt from preparative HPLC. $^1$HNMR (CDCl$_3$) δ 7.83 (bs, 2H), 7.26 (d, J=8.7 Hz, 2H), 6.95 (d, J=9.0 Hz, 2H), 6.85 (d, J=3.0 Hz, 1H), 6.41, (d, J=3.0 Hz, 1H), 3.87 (s, 3H), 3.21-3.10 (m, 4H), 3.00-2.97 (m, 2H), 2.69-2.66 (m, 2H), 1.92 (s, 3H); MS: ESI (positive): 299 (M+H).

Example 15

3-m-Tolyl-3,4,5,6,7,8-hexahydro-9-thia-3,6-diaza-cyclopenta[a]azulene

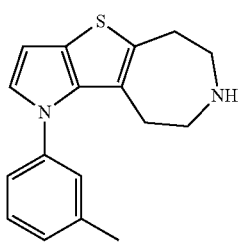 [SMILES: Cc1cccc(-n2ccc3sc4c(c32)CCNCC4)c1]

Example 15 was prepared in a similar fashion to Example 3 except 3-iodotoluene was used instead of iodobenzene (Example 3, step (a)). Product recovered as acetate salt from preparative HPLC. $^1$HNMR (CDCl$_3$) δ 8.61 (bs, 2H), 7.33 (t, J=7.8 Hz, 1H), 7.21-7.12 (m, 3H), 6.91 (d, J=3.3 Hz, 1H), 6.44 (d, J=3.0 Hz, 1H), 3.25-3.22 (m, 2H), 3.17-3.14 (m, 2H), 3.05-3.02 (m, 2H), 2.78-2.74 (m, 2H), 2.41 (s, 3H), 1.94 (s, 3H); MS: ESI (positive): 283 (M+H).

Example 16

3-(3-Methoxy-phenyl)-3,4,5,6,7,8-hexahydro-9-thia-3,6-diaza-cyclopenta[a]azulene

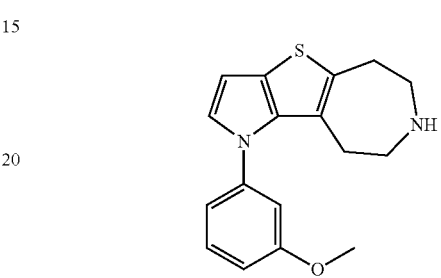

Example 16 was prepared in a similar fashion to Example 3 except 3-iodoanisole was used instead of iodobenzene (Example 3, step (a)). Product recovered as acetate salt from preparative HPLC. $^1$HNMR (CDCl$_3$) δ 8.71 (bs, 2H), 7.35 (t, J=8.1 Hz, 1H), 6.95-6.91 (m, 3H), 6.89-6.87 (m, 1H), 6.45 (d, J=3.0 Hz, 1H), 3.83 (s, 3H), 3.26-3.22 (m, 2H), 3.17-3.14 (m, 2H), 3.06-3.03 (m, 2H), 2.82-2.78 (m, 2H), 1.94 (s, 3H); MS: ESI (positive): 299 (M+H).

Example 17

3-(3-Chloro-phenyl)-3,4,5,6,7,8-hexahydro-9-thia-3,6-diaza-cyclopenta[a]azulene

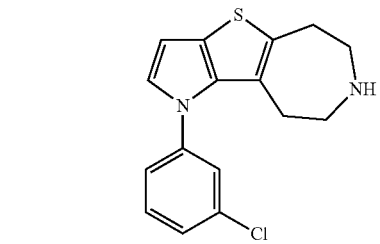 [SMILES: Clc1cccc(-n2ccc3sc4c(c32)CCNCC4)c1]

Example 17 was prepared in a similar fashion to Example 3 except 1-chloro-3-iodobenzene was used instead of iodobenzene (Example 3, step (a)). Product recovered as acetate salt from preparative HPLC. $^1$HNMR (CDCl$_3$) δ 8.52 (bs, 2H), 7.40-7.36 (m, 3H), 7.27-7.23 (m, 1H), 6.90 (d, J=3.0, 1H), 6.47 (d, J=3.0 Hz, 1H), 3.26-3.22 (m, 2H), 3.17-3.14 (m, 2H), 3.07-3.04 (m, 2H), 2.80-2.76 (m, 2H), 1.94 (s, 3H); MS: ESI (positive): 303 (M+H).

Example 18

3-(3-Methoxy-benzyl)-3,4,5,6,7,8-hexahydro-9-thia-3,6-diaza-cyclopenta[a]azulene

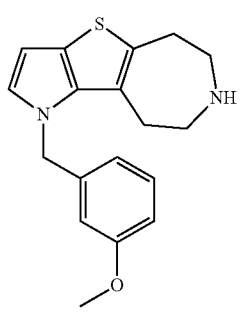 [SMILES: COc1cccc(Cn2ccc3sc4c(c32)CCNCC4)c1]

Example 18 was prepared in a similar fashion to Example 2 except 3-methoxybenzyl bromide was used instead of ethyl bromide (Example 2, step (a)). Product recovered as acetate salt from preparative HPLC. $^1$HNMR (CDCl$_3$) δ 7.65 (bs, 2H), 7.21 (t, J=7.8 Hz, 1H), 6.82 (d, J=3.0 Hz, 1H), 6.77 (dd, J=8.4 Hz, J=2.1 Hz, 1H), 6.55-6.50 (m, 2H), 6.33 (d, J=3.0 Hz, 1H), 5.28 (s, 2H), 3.74 (s, 3H), 3.13-3.10 (m,2H), 3.06-3.03 (m, 2H), 2.92-2.90 (m, 2H), 2.84-2.81 (m, 2H), 1.90 (s, 3H); MS: ESI (positive): 313 (M+H).

Example 19

3-(4-Methoxy-benzyl)-3,4,5,6,7,8-hexahydro-9-thia-3,6-diaza-cyclopenta[a]azulene

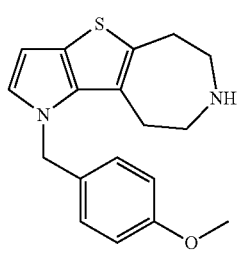 [SMILES: COc1ccc(Cn2ccc3sc4c(c32)CCNCC4)cc1]

Example 19 was prepared in a similar fashion to Example 2 except 4-methoxybenzyl chloride was used instead of ethyl bromide (Example 2, step (a)). $^1$HNMR (CDCl$_3$) δ 6.94 (d, J=8.4, 2H), 6.84-6.77 (m, 3H), 6.31 (d, J=3.0 Hz, 1H), 5.27 (s, 2H), 3.77 (s, 3H), 3.00-2.97 (m, 2H), 2.92-2.89 (m, 2H), 2.78-2.77 (m, 4H), 1.72 (bs, 1H); MS: ESI (positive): 313 (M+H).

Example 20

3-Cyclohexylmethyl-3,4,5,6,7,8-hexahydro-9-thia-3,6-diaza-cyclopenta[a]azulene

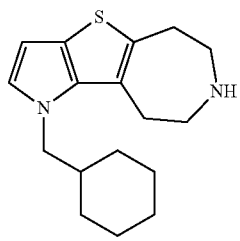 [SMILES: c1cn(CC2CCCCC2)c2c3c(sc12)CCNCC3]

Example 20 was prepared in a similar fashion to Example 2 except 4-methoxybenzyl chloride was used instead of ethyl bromide (Example 2, step (a)). $^1$HNMR (CDCl$_3$) δ 6.67 (d, J=3.0 Hz, 1H), 6.21 (d, J=3.0 Hz, 1H), 3.87 (d, J=6.9 Hz, 2H), 3.06-3.03 (m, 4H), 3.00-2.93 (m, 4H), 1.90 (bs, 1H), 1.73-1.59 (m, 6H), 1.20-1.14 (m, 3H), 0.995-0.923 (m, 2H); MS: ESI (positive): 289 (M+H).

Example 21

3-Naphthalen-1-ylmethyl-3,4,5,6,7,8-hexahydro-9-thia-3,6-diaza-cyclopenta[a]azulene

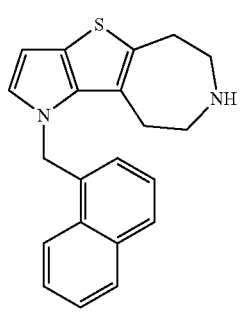 [SMILES: c1ccc2c(Cn3ccc4sc5c(c43)CCNCC5)cccc2c1]

Example 21 was prepared in a similar fashion to Example 2 except 1-(chloromethyl)napthalene was used instead of ethyl bromide (Example 2, step (a)). $^1$HNMR (CDCl$_3$) δ 7.98-7.90 (m, 2H), 7.77 (d, J=8.1 Hz, 1H), 7.60-7.55 (m, 2H), 7.34 (t, J=7.5, 1H), 6.77-6.73 (m, 2H), 6.37 (d, J=3.0 Hz, 1H), 5.79 (s, 2H), 3.00-2.91 (m, 4H), 2.64 (d, 4H), 1.74 (bs, 1H); MS: ESI (positive): 333 (M+H).

Example 22

3-(2,3-Dichloro-benzyl)-3,4,5,6,7,8-hexahydro-9-thia-3,6-diaza-cyclopenta[a]azulene

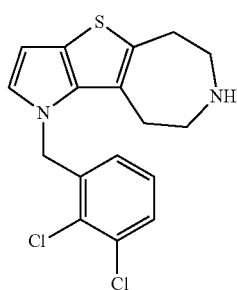 [SMILES: Clc1cccc(Cn2ccc3sc4c(c32)CCNCC4)c1Cl]

Example 22 was prepared in a similar fashion to Example 2 except 2,3-dichlorobenzyl bromide was used instead of ethyl bromide (Example 2, step (a)). Product recovered as acetate salt from preparative HPLC. $^1$HNMR (CDCl$_3$) δ 8.12 (bs, 2H), 7.38 (d, J=7.2 Hz, 1H), 7.07 (t, J=7.8 Hz, 1H), 6.80 (d, J=3.0 Hz, 1H), 6.38 (d, J=3.0 Hz, 1H), 6.34 (d, J=7.8 Hz, 1H), 5.36 (s, 2H), 3.18-3.07 (m, 4H), 2.92-2.79 (m, 4H), 1.92 (s, 3H); MS: ESI (positive): 351 (M+H).

Example 23

3-(3,4-Dichloro-benzyl)-3,4,5,6,7,8-hexahydro-9-thia-3,6-diaza-cyclopenta[a]azulene

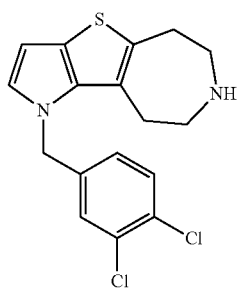 [SMILES: Clc1ccc(Cn2ccc3sc4c(c32)CCNCC4)cc1Cl]

Example 23 was prepared in a similar fashion to Example 2 except 3,4-dichlorobenzyl bromide was used instead of ethyl bromide (Example 2, step (a)). Product recovered as acetate salt from preparative HPLC. $^1$HNMR (CDCl$_3$) δ 7.65 (bs, 2H), 7.37 (d, J=8.1 Hz, 1H), 7.10 (d, J=2.1 Hz, 1H), 6.80 (d, J=3.0 Hz, 1H), 6.76 (dd, J=8.4 Hz, 2.1 Hz, 1H), 6.37 (d, J=3.0 Hz, 1H), 5.26 (s, 2H), 3.20-3.06 (m, 4H), 2.97-2.90 (m, 4H), 1.94 (s, 3H); MS: ESI (positive): 351 (M+H).

Example 24

3-Quinolin-8-ylmethyl-3,4,5,6,7,8-hexahydro-9-thia-3,6-diaza-cyclopenta[a]azulene

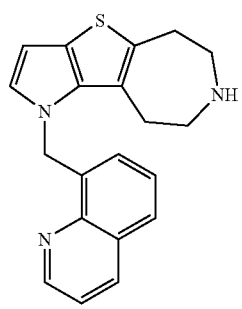

Example 24 was prepared in a similar fashion to Example 2 except 8-(bromomethyl)quinoline was used instead of ethyl bromide (Example 2, step (a)). $^1$HNMR (CDCl$_3$) δ 8.97 (dd, J=3.9 Hz, 1.8 Hz, 1H), 8.20 (dd, J=8.4 Hz, 1.8 Hz, 1H), 7.72 (d, J=8.1 Hz, 1H), 7.49 (dd, J=8.4 Hz, 4.2 Hz, 1H), 7.40 (t, J=7.8 Hz, 1H), 6.90-6.87 (m, 2H), 6.40 (d, J=2.7 Hz, 1H), 6.03 (s, 2H), 2.98-2.89 (m, 4H), 2.63-2.56 (m, 4H), 1.88 (bs, 1H); MS: ESI (positive): 334 (M+H).

Example 25

3-Isoquinolin-5-ylmethyl-3,4,5,6,7,8-hexahydro-9-thia-3,6-diaza-cyclopenta[a]azulene

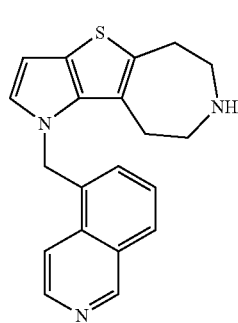 [SMILES: c1cc(Cn2ccc3sc4c(c32)CCNCC4)c2ccncc2c1]

Example 25 was prepared in a similar fashion to Example 2 except 5-bromomethyl-isoquinoline was used instead of ethyl bromide (Example 2, step (a)). $^1$HNMR (CDCl$_3$) δ 9.32 (s, 1H), 8.64 (d, J=5.7 Hz, 1H), 7.91 (d, J=8.1 Hz, 1H), 7.75 (d, J=6.0 Hz, 1H), 7.48 (t, J=7.5 Hz, 1H), 6.94 (d, J=7.2 Hz, 1H), 6.78 (d, J=3.0 Hz, 1H), 6.39 (d, J=3.0 Hz, 1H), 5.75 (s, 2H), 3.01-2.91 (m, 4H), 2.62 (s, 4H); MS: ESI (positive): 334 (M+H).

Example 26

3-Isoquinolin-1-ylmethyl-3,4,5,6,7,8-hexahydro-9-thia-3,6-diaza-cyclopenta[a]azulene

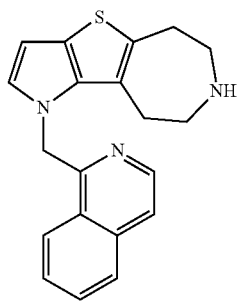

Example 26 was prepared in a similar fashion to Example 2 except 1-bromomethyl-isoquinoline was used instead of ethyl bromide (Example 2, step (a)). $^1$HNMR (CDCl$_3$) δ 8.47 (d, J=5.7 Hz, 1H), 8.02 (d, J=8.4 Hz, 1H), 7.87 (d, J=8.1 Hz, 1H), 7.70 (t, J=6.9 Hz, 1H), 7.60 (d, J=6.6 Hz, 2H), 6.73 (d, J=2.7 Hz, 1H), 6.32 (d, J=3.0 Hz, 1H), 5.93 (s, 2H), 3.02-2.99 (m, 2H), 2.94-2.86 (m, 4H), 2.80-2.77 (m, 2H), 1.73 (s, 1H); MS: ESI (positive): 334 (M+H).

Functional Potency of Compounds at 5HT$_{2c}$

Agonist potency of compounds was evaluated using the functional assay described below and the data are shown in Table 1.

Cell Culture

5-HT$_2$ Cell lines: HEK 293 EBNA stably transfected cell lines expressing the VSV or INI isoform of human 5HT$_{2c}$ receptor (Genbank accession No. U49516), human 5-HT$_{2A}$ (Genbank accession No. X57830), or human 5-HT$_{2B}$ (Genbank accession No. NM_000867) were cultured in DMEM containing 10% dialysed FBS, 1% Penicillin/Streptomycin/L-Glutamine, and 7 μg/ml blasticidin at 37° C. in 5% CO$_2$ atmosphere.

Phosphotidyl Inositol Turnover Assay

The IP-One Tb kit (CisBio, cat #62IPAPEC) was used to perform direct quantitative measurements of myo-Inositol 1-Phosphate.

HEK 293 EBNA cells expressing human 5HT$_2$ receptor of interest were harvested from T-175 cell culture flasks. Cells were washed 1× with PBS and resuspended in 1×IP1 Stimulation buffer (kit provided: 10 mM Hepes pH 7.4, 1 mM CaCl$_2$, 0.5 mM MgCl$_2$, 4.2 mM KCl, 146 mM NaCl, 5.5 mM glucose, 50 mM LiCl). Test compounds were serially diluted at 2× final concentration in 1×IP1 Stimulation buffer over the dose range 1×10$^{-11}$M-1×10$^{-4}$M. Compounds were added to a white, non-binding surface 384-well plate, each dose tested in triplicate. Cell treatment was initiated by adding cells at 2×10$^4$ cells/well to compounds plated in 384-well plate. For 5-HT$_{2C}$ VSV and INI cell lines, plates were incubated at 37° C., 5% CO$_2$ for 30 minutes. For 5-HT$_{2A}$ and 5-HT$_{2B}$ cell lines, plates were incubated for 40 minutes. Cell stimulation was terminated by addition of IP-One Tb lysis buffer (kit provided-proprietary) containing IP1-d2 conjugate and subsequent addition of anti-IP1 cryptate Tb conjugate also diluted in IP-One Tb lysis buffer. Plates were incubated in the dark for 1 hr R.T. 15 μL/well of reaction mixtures were transferred to a low-volume 384-well Proxiplate (Perkin Elmer) and time-resolved fluorescence (TRF) signals were measured using an AnalystHT Multi-mode plate reader (Molecular Devices)—TRF was measured at 665 nM and 620 nM emission wavelengths.

Data Analysis

All data were analyzed by nonlinear least square curve fitting using Prism 5.0 software. Agonist stimulation of IP1 TRF ratio (TRF ratio=(665 nm/625 nm)*1×10$^4$) was fitted to sigmoidal dose response using equation Y=Bottom+(Top-Bottom)/(1+10 ʌ((X−Log IC$_{50}$))), where X is the logarithm of concentration of compounds and Y is the TRF ratio.

TABLE 1

| Compound | EC$_{50}$ at 5HT$_{2c}$ (VSV Isoform) |
|---|---|
| | <10 nM |
| | <100 nM |
| | <10 nM |
| | <10 nM |
| | <1000 nM |

TABLE 1-continued
| Compound | EC$_{50}$ at 5HT$_{2c}$ (VSV Isoform) |
|---|---|
| 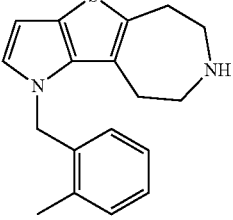 | <10 nM |
| 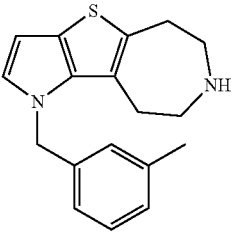 [SMILES: Cc1cccc(Cn2ccc3sc4c(c32)CCNCC4)c1] | <10 nM |
| 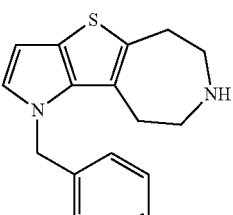 | <10 nM |
| 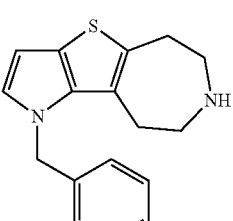 | <10 nM |
| 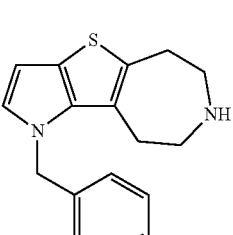 | <10 nM |
| 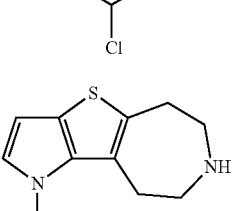 | <10 nM |
| 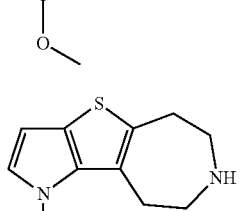 | <100 nM |
| 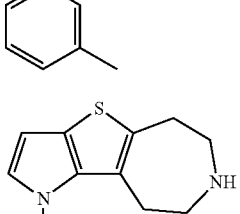 | <100 nM |
| 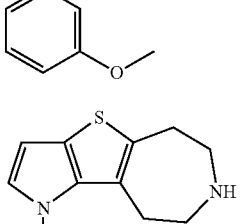 | <100 nM |
| 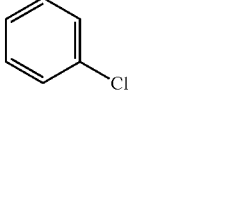 | <100 nM |
| 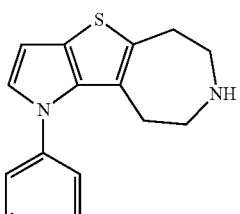 | <1000 nM |
| 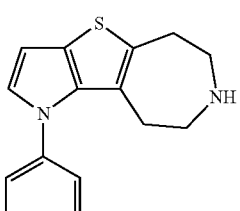 | <100 nM |

TABLE 1-continued
| Compound | EC$_{50}$ at 5HT$_{2c}$ (VSV Isoform) |
|---|---|
| 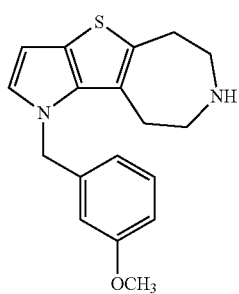 [SMILES: Clc1cccc(Cn2ccc3sc4c(c32)CCNCC4)c1] | <10 nM |
| 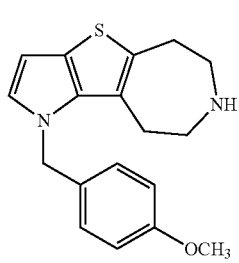 [SMILES: COc1ccc(Cn2ccc3sc4c(c32)CCNCC4)cc1] | <100 nM |
| 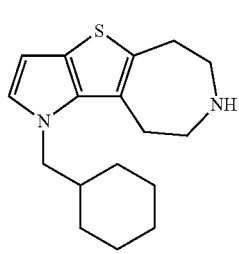 [SMILES: c1cn(CC2CCCCC2)c2c3c(sc12)CCNCC3] | <100 nM |
| 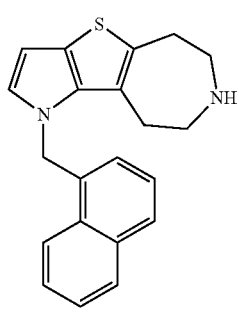 [SMILES: c1ccc2c(Cn3ccc4sc5c(c43)CCNCC5)cccc2c1] | <10 nM |
| 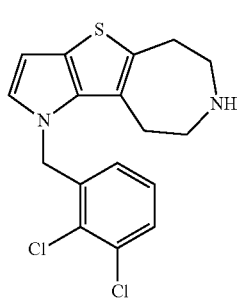 [SMILES: Clc1cccc(Cn2ccc3sc4c(c32)CCNCC4)c1Cl] | <10 nM |
TABLE 1-continued
| Compound | EC$_{50}$ at 5HT$_{2c}$ (VSV Isoform) |
|---|---|
| 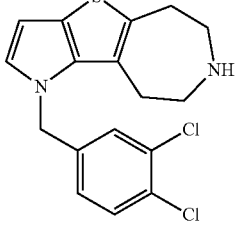 | <10 nM |
| 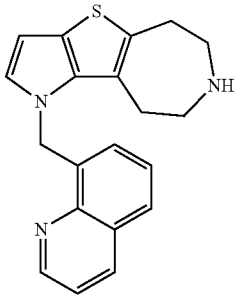 | <100 nM |
| 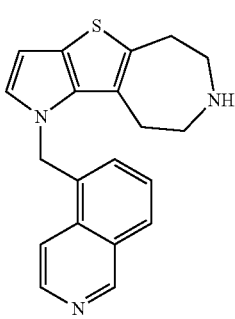 [SMILES: c1cc(Cn2ccc3sc4c(c32)CCNCC4)c2ccncc2c1] | <10 nM |
| 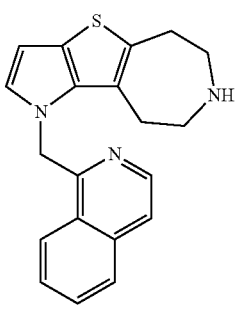 [SMILES: c1ccc2c(Cn3ccc4sc5c(c43)CCNCC5)nccc2c1] | <10 nM |
The invention claimed is:
1. A compound of the formula
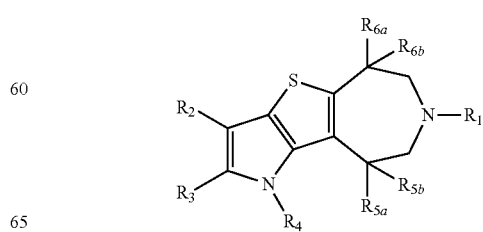

where
- $R_1$ is selected from the group consisting of H, alkyl, perhaloalkyl, alkanoyl, $C_{1-8}$ alkylaryl, and $C_{1-8}$ alkylheteroaryl;
- $R_2$ and $R_3$ are independently selected from the group consisting of H, halogen, $C_{1-8}$ alkyl, $C_{2-8}$ alkenyl, $C_{2-8}$ alkynyl, perhalo alkyl, CN, $OR_8$, $NR_7R_8$, $SR_7$, $OCOR_9$, $CONR_7R_8$, $NR_7COR_9$, $NR_7CO_2R_9$, $SO_2NR_7R_8$, $SO_2R_9$, $NR_7SO_2R_9$, aryl, heteroaryl, $C_{1-8}$ alkylaryl, and $C_{1-8}$ alkylheteroaryl;
- $R_4$ is selected from the group consisting of H, $C_{1-8}$ alkyl, $C_{2-8}$ alkenyl, $C_{2-8}$ alkynyl, perhaloalkyl, $CONR_7R_8$, $COR_5$, $SO_2R_9$, aryl, heteroaryl, $C_{1-8}$ alkylaryl, and $C_{1-8}$ alkylheteroaryl;
- $R_{5a}$ and $R_{5b}$ are independently selected from the group consisting of H, $C_{1-8}$alkyl, $OR_7$, aryl, and heteroaryl; or $R_{5a}$ and $R_{5b}$ taken together are —$CH_2CH_2$—;
- $R_{6a}$ and $R_{6b}$ are independently selected from the group consisting of H, $C_{1-8}$alkyl, $OR_7$, aryl, and heteroaryl; or $R_{6a}$ and $R_{6b}$ taken together are —$CH_2CH_2$—;
- $R_7$ is selected from the group consisting of H, $C_{1-8}$alkyl, $C_{2-8}$ alkenyl, $C_{2-8}$ alkynyl, perhaloalkyl, $C_{1-8}$ alkyl-O—$C_{1-8}$ alkyl, aryl, heteroaryl, $C_{1-8}$ alkyl-O-aryl, $C_{1-8}$ alkyl-O-heteroaryl, $C_{1-8}$ alkylaryl, and $C_{1-8}$ alkylheteroaryl;
- $R_8$ is selected from the group consisting of H, $C_{1-8}$alkyl, $C_{2-8}$ alkenyl, $C_{2-8}$ alkynyl, perhaloalkyl, $C_{1-8}$ alkyl-O—$C_{1-8}$ alkyl, aryl, heteroaryl, $C_{1-8}$ alkyl-O-aryl, $C_{1-8}$ alkyl-O-heteroaryl, $C_{1-8}$ alkylaryl, and $C_{1-8}$ alkylheteroaryl; and
- $R_9$ is selected from the group consisting of $C_{1-8}$ alkyl, $C_{2-8}$ alkenyl, $C_{2-8}$ alkynyl, perhaloalkyl, $C_{1-8}$ alkyl-O—$C_{1-8}$ alkyl, aryl, heteroaryl, $C_{1-8}$ alkyl-O-aryl, $C_{1-8}$ alkyl-O-heteroaryl, $C_{1-8}$ alkylaryl, and $C_{1-8}$ alkylheteroaryl, or a pharmaceutically acceptable salt thereof.

2. A compound according to claim 1 wherein $R_1$ is H.

3. A compound according to claim 1 wherein $R_1$ is alkanoyl.

4. The compound according to claim 1, wherein $R_1$, $R_2$, $R_3$, $R_{5a}$, $R_{5b}$, $R_{6a}$ and $R_{6b}$ are all H, and $R_4$ is selected from the group consisting of H, $C_{1-8}$ alkyl, $C_{2-8}$ alkenyl, $C_{2-8}$ alkynyl, perhaloalkyl, aryl, heteroaryl, $C_{1-8}$ alkylaryl, and $C_{1-8}$ alkylheteroaryl.

5. The compound according to claim 1, wherein $R_4$ is selected from the group consisting of H, $C_{1-8}$ alkyl, $C_{2-8}$ alkenyl, $C_{2-8}$ alkynyl, perhaloalkyl, aryl, heteroaryl, $C_{1-8}$ alkylaryl, and $C_{1-8}$ alkylheteroaryl, and further wherein said aryl and/or $C_{1-8}$ alkylaryl are substituted with one to three of the substituents selected from the group consisting of H, halo, CN, $NO_2$, $CF_3$, $N_3$, $C_{1-6}$ alkyl, OH, $NR_7R_8$, $OC_{1-6}$ alkyl, $OR_7$, $C(=O)NR_7R_8$, $C(=S)N_7R_8$, tetrazoyl, triazoyl, amidinyl, guanidinyl, thioguanidinyl, cyanoguanadinyl, and aryl.

6. The compound according to claim 1, wherein $R_4$ is selected from the group consisting of H, $C_{1-8}$ alkyl, $C_{2-8}$ alkenyl, $C_{2-8}$ alkynyl, perhaloalkyl, aryl, heteroaryl, $C_{1-8}$ alkylaryl, and $C_{1-8}$ alkylheteroaryl, and further wherein said heteroaryl and/or $C_{1-8}$ alkylheteroaryl are substituted with one to three of the substituents selected from the group consisting of H, halo, CN, $NO_2$, $CF_3$, $N_3$, $C_{1-6}$ alkyl, OH, $NR_7R_8$, $OC_{1-6}$ alkyl, $OR_7$, $C(=O)NR_7R_8$, $C(=S)N_7R_8$, tetrazoyl, triazoyl, amidinyl, guanidinyl, thioguanidinyl, cyanoguanadinyl, and aryl.

7. A compound according to claim 1 selected from the group consisting of 3,4,5,6,7,8-H exahydro-9-thia-3,6-diaza-cyclopentara[a]azulene;
3-Ethyl-3,4,5,6,7,8-hexahydro-9-thia-3,6-diaza-cyclopenta[a]azulene;
3-Phenyl-3,4,5,6,7,8 -hexahydro-9-thia-3,6-diaza-cyclopenta[a]azulene;
3-Benzyl-3,4,5,6,7,8-hexahydro-9-thia-3,6-diaza-cyclopenta[a]azulene;
3-(4-Chloro-phenyl)-3,4,5,6,7,8-hexahydro-9-thia-3,6-diaza-cyclopenta[a]azulene;
3-(2-Methyl-benzyl)-3,4,5,6,7,8-hexahydro-9-thia-3,6-diaza-cyclopenta[a]azulene;
3-(3 -Methyl-benzyl)-3,4,5,6,7,8-hexahydro-9-thia-3,6-diaza-cyclopenta[a]azulene;
3-(4-Methyl-benzyl)-3,4,5,6,7,8-hexahydro-9-thia-3,6-diaza-cyclopenta[a]azulene;
3-Naphthalen-2-ylmethyl-3,4,5,6,7,8-hexahydro-9-thia-3,6-diaza-cyclopenta[a]azulene;
3-(2-Chloro-benzyl)-3,4,5,6,7,8-hexahydro-9-thia-3,6-diaza-cyclopenta[a]azulene;
3-(3-Chloro-benzyl)-3,4,5,6,7,8-hexahydro-9-thia-3,6-diaza-cyclopenta[a]azulene;
3-(4-Chloro-benzyl)-3,4,5,6,7,8-hexahydro-9-thia-3,6-diaza-cyclopenta[a]azulene;
3-p-Tolyl-3,4,5,6,7,8-hexahydro-9-thia-3,6-diaza-cyclopenta[a]azulene;
3-(4-Methoxy-phenyl)-3,4,5,6,7,8 -hexahydro-9-thia-3,6-diaza-cyclopenta[a]azulene;
3-m-Tolyl-3,4,5,6,7,8-hexahydro-9-thia-3,6-diaza-cyclopenta[a]azulene;
3-(3-Methoxy-phenyl)-3,4,5,6,7,8-hexahydro-9-thia-3,6-diaza-cyclopenta [a]azulene;
3-(3-Chloro-phenyl)-3,4,5,6,7,8-hexahydro-9-thia-3,6-diaza-cyclopenta [a]azulene;
3-(3-Methoxy-benzyl)-3,4,5,6,7,8-hexahydro-9-thia-3,6-diaza-cyclopenta[a]azulene;
3-(4-Methoxy-benzyl)-3,4,5,6,7,8-hexahydro-9-thia-3,6-diaza-cyclopenta[a]azulene;
3-Cyclohexylmethyl-3,4,5,6,7,8-hexahydro-9-thia-3,6-diaza-cyclopenta[a]azulene;
3-Naphthalen-1-ylmethyl-3,4,5,6,7,8-hexahydro-9-thia-3,6-diaza-cyclopenta[a]azulene;
3-(2,3-Dichloro-benzyl)-3,4,5,6,7,8-hexahydro-9-thia-3,6-diaza-cyclopenta[a]azulene;
3-(3,4-Dichloro-benzyl)-3,4,5,6,7,8-hexahydro-9-thia-3,6-diaza-cyclopenta[a]azulene;
3-Quinolin-8-ylmethyl-3,4,5,6,7,8-hexahydro-9-thia-3,6-diaza-cyclopenta[a]azulene;
3-Isoquinolin-5-ylmethyl-3,4,5,6,7,8-hexahydro-9-thia-3,6-diaza-cyclopenta[a]azulene; and
3-Isoquinolin-1-ylmethyl-3,4,5,6,7,8-hexahydro-9-thia-3,6-diaza-cyclopenta[a]azulene.

8. A pharmaceutical composition comprising at least one compound of claim 1 and a pharmaceutically acceptable carrier.

9. A method of treating a disease, disorder and/or condition selected from the group consisting of obesity, attention deficit disorder, migraine, Type II diabetes, and epilepsy in a patient in need thereof comprising administering an effective amount of at least one compound of claim 1 to said patient.

* * * * *